United States Patent
Leroux et al.

(10) Patent No.: US 11,713,376 B2
(45) Date of Patent: Aug. 1, 2023

(54) TRANSMEMBRANE PH-GRADIENT POLYMERSOMES FOR THE QUANTIFICATION OF AMMONIA IN BODY FLUIDS

(71) Applicant: ETH ZURICH, Zurich (CH)

(72) Inventors: Jean-Christophe Leroux, Zurich (CH); Simon Matoori, Zurich (CH); Olha Voznyuk Wuerthinger, Zurich (CH)

(73) Assignee: ETH ZURICH, Zurich (CH)

( * ) Notice: Subject to any disclaimer, the term of this patent is extended or adjusted under 35 U.S.C. 154(b) by 597 days.

(21) Appl. No.: 16/645,763

(22) PCT Filed: Sep. 10, 2018

(86) PCT No.: PCT/IB2018/056887
§ 371 (c)(1),
(2) Date: Mar. 9, 2020

(87) PCT Pub. No.: WO2019/053578
PCT Pub. Date: Mar. 21, 2019

(65) Prior Publication Data
US 2020/0283583 A1    Sep. 10, 2020

Related U.S. Application Data

(60) Provisional application No. 62/557,256, filed on Sep. 12, 2017.

(51) Int. Cl.
*C08G 81/02* (2006.01)
*B01J 13/08* (2006.01)
(Continued)

(52) U.S. Cl.
CPC ............ *C08G 81/025* (2013.01); *B01J 13/08* (2013.01); *B01J 13/12* (2013.01); *C08K 5/19* (2013.01);
(Continued)

(58) Field of Classification Search
None
See application file for complete search history.

(56) References Cited

U.S. PATENT DOCUMENTS

| 6,835,394 B1 | 12/2004 | Discher |
|---|---|---|
| 2003/0119396 A1 | 6/2003 | Koenig et al. |

(Continued)

FOREIGN PATENT DOCUMENTS

| CN | 104771382 | 7/2015 |
|---|---|---|
| EP | 2695606 | 2/2014 |

(Continued)

OTHER PUBLICATIONS

International Preliminary Report on Patentability received for PCT Patent Application No. PCT/IB2018/056887, dated Mar. 26, 2020, 7 pages.

(Continued)

*Primary Examiner* — Jeffrey D Washville
(74) *Attorney, Agent, or Firm* — Faegre Drinker Biddle & Reath LLP

(57) ABSTRACT

The present invention provides polymersomes comprising amphiphilic block-copolymers and their use to quantify ammonia in samples (e.g., body fluid samples). More particularly, it provides a polymersome comprising (a) a membrane, which comprises a block copolymer of poly(styrene) (PS) and poly(ethylene oxide) (PEO), wherein the PS/PEO molecular weight ratio is higher than 1.0 and lower than 4.0; and (b) a core which encloses an acid and at least one pH-sensitive dye. Compositions, strips and kits comprising the polymersomes are also provided along with methods of quantifying ammonia in a sample using the polymersomes, compositions and kit.

23 Claims, 15 Drawing Sheets

(51) Int. Cl.
- *C08K 5/19* (2006.01)
- *C08K 5/353* (2006.01)
- *C08K 5/42* (2006.01)
- *G01N 33/84* (2006.01)
- *G01N 33/68* (2006.01)
- *B01J 13/12* (2006.01)
- *C09K 11/06* (2006.01)
- *A61K 9/127* (2006.01)

(52) U.S. Cl.
CPC .......... *C08K 5/353* (2013.01); *C08K 5/42* (2013.01); *C09K 11/06* (2013.01); *G01N 33/689* (2013.01); *G01N 33/84* (2013.01); *A61K 9/1273* (2013.01); *B01J 13/125* (2013.01); *G01N 2800/085* (2013.01)

(56) References Cited

U.S. PATENT DOCUMENTS

| | | |
|---|---|---|
| 2005/0003016 A1 | 1/2005 | Discher |
| 2005/0019265 A1 | 1/2005 | Hammer |
| 2009/0170342 A1 | 7/2009 | Kim et al. |
| 2010/0098773 A1 | 4/2010 | Hammer |
| 2011/0256225 A1 | 10/2011 | Ghoroghchian |

FOREIGN PATENT DOCUMENTS

| | | |
|---|---|---|
| JP | H06207112 A | 7/1994 |
| JP | 2014526314 A | 10/2014 |
| JP | 2016507158 A | 3/2016 |
| JP | 2016173293 A | 9/2016 |
| JP | 2016529515 A | 9/2016 |
| JP | 2017507113 A | 3/2017 |
| JP | 2022510519 A | 1/2022 |
| WO | WO200132146 | 5/2001 |
| WO | WO2006096571 | 9/2006 |
| WO | WO2007133807 | 11/2007 |
| WO | WO2009117188 | 9/2009 |
| WO | WO2010017177 | 2/2010 |
| WO | WO2010148395 | 12/2010 |
| WO | WO2010148653 | 12/2010 |
| WO | WO2012007567 | 1/2012 |
| WO | WO2012094679 | 7/2012 |
| WO | WO2012140415 | 10/2012 |
| WO | WO2013025801 | 2/2013 |
| WO | WO2014130761 | 8/2014 |
| WO | 2015/031911 A1 | 3/2015 |
| WO | 2015052579 A1 | 4/2015 |
| WO | WO2015050869 | 4/2015 |
| WO | WO2015059180 | 4/2015 |

OTHER PUBLICATIONS

International Search Report and Written Opinion received for PCT Patent Application No. PCT/IB2018/056887, dated Dec. 19, 2018, 9 pages.
Bajaj et al. 190 AST-120 (Spherical Carbon Adsorbent) in Covert Hepatic Encephalopathy: Results of the Astute Trial J. Hepatol 2013; 58:S84.
Blankenstein T et al. (2015). Point-of-care (POC) diagnosis of bacterial vaginosis (BV) using VGTest™ ion mobility spectrometry (IMS) in a routine ambulatory care gynecology clinic. Archives of gynecology and obstetrics 292(2), 355-362.
Bosoi et al. AST-120 (spherical carbon adsorbent) lowers ammonia levels and attenuates brain edema in bile duct-ligated rats. Hepatology 2011; 53:1995-2002.
Cashman JR et al. (1999) In-vitro and in-vivo studies inhibition of human flavin-containing monooxygenase form 3 (FMO3) in the presence of dietary indoles. Biochem Pharmacol 58, 1047-1055.
Cashman JR et al. (2003). Biochemical and clinical aspects of the human flavin-containing monooxygenase form 3 (FMO3) related to trimethylaminuria. Current drug metabolism, 4(2), 151-170.
CN 104771382 Zhang Jul. 15, 2015 English translation.
Danks DM et al. (1976) Trimethylaminuria: diet does not always control the fishy odor. The New England Journal of Medicine, 295(17), 962-962.
Davankov and Tsyurupa Structure and properties of hypercrosslinked polystyrene—the first representative of a new class of polymer networks Reactive Polymers 1990;13:27-42.
Discher et al. Emerging applications of polymersomes in delivery: From molecular dynamics to shrinkage of tumors Progress in Polymer Science 2007, 32(8-9), pp. 838-857.
Ernenweim et al. Self-Assembling Amphiphilic Hyperbranched Polyglycerol-Polystyrene Copolymers for Encapsulation Macromolecular Chemistry and Physics 2015 216(16): 1729-1736.
Forster et al. Liposome-supported peritoneal dialysis in the treatment of severe hyperammonemia: An investigation on potential interactions J Control Release. May 28, 2018;278:57-65.
Hayward et al. Dewetting Instability during the Formation of Polymersomes from Block-Copolymer-Stabilized Double Emulsions Langmuir 2006, 22(10): 4457-4461.
Hocine et al. Polymersomes with PEG corona: structural changes and controlled release induced by temperature variation. Langmuir. Feb. 5, 2013;29(5):1356-69.
Leevy et al. Hospitalizations during the use of rifaximin versus lactulose for the treatment of hepatic encephalopathy. Dig Dis Sci 2007; 52:737-41.
Levy J. The effects of antibiotic use on gastrointestinal function. The American Journal of Gastroenterology, 2000, 95 (1), S8-S10.
Matoori and Leroux Recent advances in the treatment of hyperammonemia.ADDR 2015; 90:55-68.
Men et al. Methods for production of uniform small-sized polymersome with rigid membrane Polymer Chemistry 2016, 7(24):3941-4128.
Mullen et al. Rifaximin is safe and well tolerated for long-term maintenance of remission from overt hepatic encephalopathy Clin Gastroenterol Hepatol 2014;12:1390-1397.e2.
Neff et al. Update on the management of cirrhosis—focus on cost-effective preventative strategies Clinicoecon Outcomes Res. 2013; 5: 143-152.
Neuvonen and Elonen Effect of activated charcoal on absorption and elimination of phenobarbitone, carbamazepine and phenylbutazone in man Eur J Clin Pharmacol 1980; 17:51-57.
Neuvonen and Olkkola Oral activated charcoal in the treatment of intoxications. Role of single and repeated doses Med Toxicol 1988; 3:33-58.
Poorrad Review article: the burden of hepatic encephalopathy. Aliment Pharmacol Ther. 2007; 25: 3-9.
Rose Ammonia-Lowering Strategies for the Treatment of Hepatic Encephalopathy Clinical Pharmacology & Therapeutics 2012; 92:321-331.
Schulman et al. A multicenter, randomized, double-blind, placebo-controlled, dose-ranging study of AST-120 (Kremezin) in patients with moderate to severe CKD Am J Kidney Dis 2006; 47:565-577.
Song et al. Preparation of Surfactant-Resistant Polymersomes with Ultrathick Membranes through RAFT Dispersion Polymerization ACS Appl Mater Interfaces. 2016, 8(27):17033-7.
Stepanova et al. In-hospital mortality and economic burden associated with hepatic encephalopathy in the United States from 2005 to 2009Clin Gastroenterol Hepatol 2012; 10:1034-1041.e1.
Szoka and Papahadjopoulos. Procedure for preparation of liposomes with large internal aqueous space and high capture by reverse-phase evaporation PNAS 1978; 75:4194-4198.
Tang WW et al. (2013). Intestinal microbial metabolism of phosphatidylcholine and cardiovascular risk. New England Journal of Medicine 368(17), 1575-1584.
Tang WW et al. (2015). Gut microbiota-dependent trimethylamine N-oxide (TMAO) pathway contributes to both development of renal insufficiency and mortality risk in chronic kidney disease Circulation research 116(3), 448-455.
Todd WA (1979). Psychosocial problems as the major complication of an adolescent with trimethylaminuria. The Journal of pediatrics, 94(6), 936-937.

(56) References Cited

OTHER PUBLICATIONS

Treacy E et al. (1995). Trimethylaminuria, fish odour syndrome: a new method of detection and response to treatment with metronidazole. Journal of inherited metabolic disease, 18(3), 306-312.

Van Dongen A Block Copolymer for Functionalisation of Polymersome Surfaces 2008, 29(40): 321-325.

Vilstrup et al. Hepatic encephalopathy in chronic liver disease: 2014 Practice Guideline by the American Association for the Study of Liver Diseases and the European Association for the Study of the Liver.Hepatology 2014; 60:715-735.

Wang Z et al. (2011). Gut flora metabolism of phosphatidylcholine promotes cardiovascular disease. Nature 472 (7341), 57-63.

Wang Z et al. (2015). Non-lethal inhibition of gut microbial trimethylamine production for the treatment of atherosclerosis. Cell 163(7), 1585-1595.

Wilcken B (1993). Acid soaps in the fish odour syndrome. BMJ: British Medical Journal, 307(6917), 1497.

Wise PM et al. (2011). Individuals reporting idiopathic malodor production: demographics and incidence of trimethylaminuria. The American journal of medicine 124(11), 1058-1063.

Yamazaki H et al. (2004). Effects of the dietary supplements, activated charcoal and copper chlorophyllin, on urinary excretion of trimethylamine in Japanese trimethylaminuria patients. Life sciences, 74(22), 2739-2747.

Yeung CK et al. (2007). Functional characterization of genetic variants of human FMO3 associated with trimethylaminuria. Archives of biochemistry and biophysics, 464(2), 251-259.

Yuan et al. The "crew-cut" aggregates of polystyrene-b-poly(ethylene oxide)-b-polystyrene triblock copolymers in aqueous media European Polymer Journal 2003, 39(4):767-776.

Baliga et al. Salivary pH: a Diagnostic Biomarker. Journal of Indian Society of Periodontology 2013, 17(4): 461-465.

Mortimer et al., Chemie, 12nd edition, Thieme, 2015.

Japanese Patent Office; Japanese Office Action; Japanese Application No. 2020-506727; dated Mar. 4, 2022; 5 pages.

Katano, Yumi et al.; Kangoroo! Nursing Knowledge that can be Used in the Field: Movement of Materials Inside and Outide Cells (1); Basic Functions of Cells: Diffusion and Simple Diffusion; htttps://www.kango-roo.com/learning/2073/; Feb. 14, 2016.

Okouchi, Naohiko; Ammonia and Ammonium, Kagaku; vol. 87 No. 12, p. 1081-1082; Dec. 2017.

Bolotin, Elijah M. et al.; Ammonium Sulfate Gradients for Efficient and Stable Remote Loading of Amphipathic Weak Bases into Liposomes and Ligandoliposomes; Journal of Liposome Research; vol. 4 No. 1; pp. 455-479; 1994.

Giacalone, Giovanna et al.; Liposome-supported peritoneal dialysis in the treatment of severe hyperammonemia: An investigation on potential interactions; Journal of Controlled Release; vol. 278; pp. 57-65; May 28, 2018.

Lai, Chun-Ze et al.; Autonomous Optofluidic Chemical Analyzers for Marine Applications: Insights from the Submersible Autonomous Moored Instruments (SAMI) for pH and pCO2; Frontier in Marine Science; vol. 4; Article No. 438; Jan. 19, 2018.

TRANSMEMBRANE PH-GRADIENT POLYMERSOMES FOR THE QUANTIFICATION OF AMMONIA IN BODY FLUIDS

CROSS-REFERENCE TO RELATED APPLICATIONS

This application is a National Entry Application of PCT application no PCT/IB2018/056887 filed on Sep. 10, 2018 and published in English under PCT Article 21(2), which itself claims the benefit of U.S. provisional application Ser. No. 62/557,256 filed on Sep. 12, 2017. All documents referenced above and their contents are incorporated herein by reference in their entireties.

FIELD OF THE INVENTION

The present invention relates to the composition and use of transmembrane pH-gradient polymersomes for quantifying ammonia in body fluids (e.g., serum, plasma, and saliva). More specifically, the present invention is concerned with quantifying this molecule to e.g., diagnose and monitor diseases or conditions such as hepatic encephalopathy.

BACKGROUND OF THE INVENTION

Ammonia ($NH_3$) is a neurotoxic endogenous metabolite which accumulates in patients suffering from various diseases and conditions (e.g., impaired liver function (e.g., due to liver cirrhosis, acute liver failure, portosystemic shunting, inborn errors of ammonia metabolism) (Matoori and Leroux ADDR 2015; 90:55-68)) or undergo certain treatments. Ammonia may also accumulate in other environments, such as soil and wastewaters.

Ammonia in Body Fluids

High blood ammonia levels (hyperammonemia) are associated with hepatic encephalopathy (HE), a serious neuropsychiatric condition with acute and chronic manifestations potentially resulting in death (Vilstrup et al. Hepatology 2014; 60:715-735). The prevalence of HE in cirrhotic patients is high (up to 20%) (Vilstrup et al. supra; Blachier et al. Journal of Hepatology 2013; 58:593-608). This chronic disorder usually progresses from low-grade (cognitive impairment) to serious (hyperammonemic coma, in some patients with lethal outcome) symptoms (Vilstrup et al. supra). The plasma ammonia cut-off value is at 50 µM for adults and 100 µM for infants (Matoori and Leroux supra). In acute hyperammonemic crises, serum ammonia levels of more than 1.5 mM were reported (Bergmann et al. Pediatrics 2014; 133:e1072-e1076).

The quantification of ammonia in blood or plasma is an essential part of the initial diagnosis of HE and in the follow-up of HE patients. The response of the HE patients to therapeutic interventions (e.g., lactulose therapy) is partly determined based on the change in plasma ammonia levels (Vilstrup et al. supra). Furthermore, plasma ammonia levels are also measured in certain drug treatments that are associated with hyperammonemia (e.g., valproic acid therapy) (Vilstrup et al. supra).

Ammonia levels in semen have also been associated with semen quality and reduced fertility (Kim et al. 1998).

Salivary ammonia levels are mainly influenced by the urease-mediated degradation of urea to ammonia in the oral cavity, and thus could be a surrogate parameter of plasma urea. The quantification of oral ammonia was used, for instance, in patients suffering from chronic kidney disease because plasma urea levels are a marker of the success of hemodialysis, enabling caregivers to determine when the dialysis session could be terminated (Hibbard et al. Anal Chem 2013; 85: 12158-12165). As salivary ammonia concentrations are comparably high (approx. 1-8 mM, Chen et al. J Breath Res. 2014; 8:036003, FIG. 5), they cannot be evaluated by established ammonia quantification methods without prior dilution. Currently, ammonia measurements in many bodily fluids are challenging. Apart from the need for sample storage at low temperatures to prevent ammonia-generating degradation processes in the sample, the available methods for ammonia quantification have important limitations (Barsotti The Journal of Pediatrics 2001; 138: S11-S20). The Berthelot reaction, which is based on the indophenol-forming reaction of phenol, ammonia, and hypochlorite, is strongly influenced by primary amines (e.g., amino acids, proteins) due to its low selectivity (FIG. 1), which impedes its use in biological fluids. In the enzyme-based ammonia assay (e.g., Randox Ammonia Assay AM1015, Randox Laboratories Ltd, Schwyz, Switzerland), glutamate dehydrogenase converts ammonia and alpha-ketoglutarate into L-glutamate and water under the stoichiometric oxidation of NAD(P)H to NA(D)P$^+$. Due to the different absorbance spectra of NAD(P)H and NAD(P)$^+$, the reaction turnover can be followed spectrophotometrically, and the ammonia concentration can be determined. The upper limit of quantification of most commercial glutamate dehydrogenase-based assays is around 1.2 mM. Unfortunately, the enzymatic ammonia quantification method is influenced by a variety of factors (e.g., lipids, heavy metals such as zinc or iron, enzymes reacting with NAD(P)H or NAD(P)$^+$, tannins) and relies on exact timing to yield reliable results because of the strong time dependence of the enzymatic reaction (Seiden-Long et al., Clinical Biochemistry 2014; 47:1116-1120). This complicates high-throughput experiments. The PocketChem™ BA Blood Ammonia Analyzer is a strip-based system for point-of-care ammonia testing in capillary blood. When the sample penetrates the strip, it is alkalized which converts ammonium to ammonia. The ammonia subsequently crosses a hydrophobic membrane and leads to a pH change on an indicator strip, which is quantified spectrophotometrically. The PocketChem™ BA Blood Ammonia Meter PA-4140 is not widely used preclinically and clinically because of its negative constant and proportional biases, low throughput (3 minutes per measurement), and low upper limit of quantification (0.285 mM) (Goggs et al. Veterinary Clinical Pathology 2008; 37:198-206).

Other Samples

Ammonia is a frequent contaminant of soil and water (due to e.g., ammonia-containing fertilizers or industrial waste (Mook et al. Desalination 2012; 285:1-13). It is generally quantified using ammonium ion-selective electrodes (Mook et al. supra). However, cations with the same charge and a similar ionic radius (e.g., potassium) could interfere with ion-selective electrode measurements.

There is a need for alternative quantification tools for ammonia in samples including body fluids.

The present description refers to a number of documents, the content of which is herein incorporated by reference in their entirety.

SUMMARY OF THE INVENTION

This invention describes the composition and use of transmembrane pH-gradient polymersomes for quantifying (e.g., determining the concentration of) ammonia in body fluids. It uses for example polymersomes composed of amphiphilic block-copolymers (e.g. poly(styrene)-b-poly (ethylene oxide) (PS-b-PEO, also known as poly(styrene)-b-poly(ethylene glycol), PS-b-PEG)).

The increase in pH in the polymersome core resulting from the capture of ammonia is quantified using a pH-sensitive dye (e.g., pyranine (trisodium salt of 8-hydroxypyrene-1,3,6-trisulfonate i.e. HPTS trisodium salt), Lysosensor™ Yellow/Blue dextran conjugate, disodium salt of 8-aminonaphthalene-1,3,6-trisulfonate (ANTS), IRDye™ 680RD carboxylate, etc.).

Polymersomes composed of the amphiphilic block-copolymer poly(styrene)-b-poly(ethylene glycol) (PS-b-PEO) and an acidic component (see e.g., co-pending PCT application No: PCT/IB2017/054966 filed Aug. 15, 2017) were used for measuring the ammonia concentration in body fluids. To prepare the polymersomes, an organic solvent was used. The polymer was dissolved in an appropriate solvent (e.g., dichloromethane) and emulsified in an acidic solution (e.g., citric acid) or a sodium chloride solution which contained a pH-sensitive dye. After elimination of the solvent, the polymersomes were purified to remove the unencapsulated dye and, if any, other weak acid. The polymersomes then exhibited their uptake properties towards ammonia once exposed to a neutral or high pH solution. The efficacy of the polymersomes was demonstrated here by showing the quantification of ammonia in buffer as well as native and spiked serum, plasma, saliva, urine, sweat and semen (FIGS. 3-5 and 7-9).

The polymersomes of the present invention can be used for the quantification of ammonia (or, indirectly, of other biomarkers which may be transformed in vitro into a corresponding (factor of 1 or more) amount of ammonia (e.g., amino acids such as phenylalanine)). In more specific embodiments, they may be used to assay body fluids for the diagnosis of ammonia-associated diseases or disorders (e.g., hyperammonemia), follow-up of patients with an ammonia-associated disease or disorder, and for research and preclinical use. The diagnostic product of the present invention can be used in in vitro, preclinical (e.g., animal studies), and clinical studies necessitating ammonia quantification as well as in ammonia measurements in routine clinical practice. Ammonia measurements can be used for the diagnosis and staging of ammonia-related diseases or disorders and in the assessment of the response of a hyperammonemic patient to an anti-hyperammonemia treatment or the response of a patient at risk for hyperammonemia to a preventive measure. The present invention can further be used to quantify ammonia in in vitro assays, more specifically for identifying compounds which inhibit the production of ammonia.

Transmembrane pH-gradient PS-b-PEO polymersome of the present invention may advantageously show high selectivity to ammonia (FIG. 6)—presumably, but without being limited by this hypothesis, due to the impermeable nature of the highly hydrophobic polystyrene membrane—and a large detection range of at least about 0.005 mM to about 8 mM (FIGS. 2 and 13). A high upper limit of quantification would be advantageous as it would at least reduce (and may even abrogate) the need for diluting concentrated ammonia samples.

Furthermore, the kinetics of the ammonia uptake into the polymersomes are fast and independent of time (low time dependence) after 2.5 minutes' incubation at physiological pH (FIG. 2). These features enable the analysis of a high number of samples at the same time.

More specifically, in accordance with an aspect of the present invention, there are provided the following items:

Item 1. A polymersome comprising (a) a membrane, which comprises a block copolymer of poly(styrene) (PS) and poly(ethylene oxide) (PEO), wherein the PS/PEO molecular weight ratio is higher than 1.0 and lower than 4.0; and (b) a core which encloses an acid and at least one pH-sensitive dye.

Item 2. The polymersome of item 1, wherein the block copolymer is a diblock copolymer.

Item 3. The polymersome of item 1 or 2, wherein the acid is in a concentration that produces a pH between 1 and 6.5, between 2 and 6.5, between 2 and 6, between 2 and 5.5, or between 3 and 5.5, when the polymersome is hydrated.

Item 4. The polymersome of any one of items 1 to 3, wherein the acid is within an aqueous acidic solution.

Item 5. The polymersome of item 4, wherein the pH within the aqueous acidic solution is between 1 and 6.5, between 2 and 6.5, between 2 and 5.5, or between 3 and 5.5.

Item 6. The polymersome of any one of items 1 to 5, wherein the at least one pH-sensitive dye comprises a (i) hydroxypyrene; (ii) phenylpyridyloxazole; (iii) aminonaphthalene; (iv) cyanine; or (v) any pH-sensitive fluorescent derivative of any one of (i) to (iv).

Item 7. The polymersome of item 6, wherein the pH-sensitive dye comprises 8-hydroxypyrene-1,3,6-trisulfonate (HPTS), dextran-conjugated Lysosensor™ Yellow/Blue, 8-aminonaphthalene-1,3,6-trisulfonate (ANTS), or IRDye™ 680RD carboxylate.

Item 8. The polymersome of any one of items 1 to 7, wherein the acid and the at least one pH-sensitive dye are different molecules.

Item 9. The polymersome of any one of items 1 to 8, wherein the acid is a hydroxy acid, most preferably a citric acid.

Item 10. The polymersome of any one of items 1 to 7, wherein the acid and the at least one pH-sensitive dye are the same molecule.

Item 11. The polymersome of any one of items 1 to 10, prepared by a method comprising mixing an organic solvent containing the copolymer with an aqueous phase containing the acid and at least one pH-sensitive dye.

Item 12. The polymersome of item 11, wherein the organic solvent is water immiscible or partially water miscible.

Item 13. The polymersome of any one of items 1 to 12, wherein the pH-sensitive dye is a pH-sensitive fluorescence dye.

Item 14. The polymersome of any one of items 1 to 12, wherein the pH-sensitive dye is a pH-sensitive absorbance dye.

Item 15. A method of making the polymersome defined in any one of items 1 to 14, comprising:
(a) dissolving the block copolymer of PS and PEO in an organic solvent, preferably a water-immiscible or partially water-miscible organic solvent, to form a copolymer-containing organic phase;
(b) mixing the copolymer-containing organic solvent phase with an aqueous phase containing the acid and at least one pH-sensitive dye so as to form the polymersome; and
(c) removing the unencapsulated at least one pH-sensitive dye and organic solvent.

Item 16. The method of item 15, wherein the aqueous phase comprises between 0.2 to 100 mM of acid.

Item 17. A polymersome prepared by the method defined in item 15 or 16.

Item 18. The polymersome of any one of items 1 to 14 and 17, the core of which further encloses ammonia.

Item 19. A composition comprising the polymersome defined in any one of items 1 to 14 and 17, and at least one excipient.

Item 20. The composition of item 19, wherein the at least one excipient comprises a preservative, a cryoprotectant, a lyoprotectant, an antioxidant, or a combination of at least two thereof.

Item 21. The composition of item 19 or 20, wherein the composition is in a liquid or solid form.

Item 22. A strip comprising the composition defined in item 19 or 20 in solid form.

Item 23. The polymersome of any one of items 1 to 14 and 17, or the composition of any one of items 19 to 21, or the strip of item 22, for use in the quantification of ammonia in a fluid sample.

Item 24. The polymersome, composition or strip for use of item 23, wherein the sample comprises a body fluid from a subject.

Item 25. The polymersome, composition or strip for use of item 24, wherein the sample further comprises a buffer.

Item 26. The polymersome, composition or strip for use of item 24, wherein the subject (i) has an ammonia-associated disease or disorder or phenylketonuria; (ii) is suspected of having or is a likely candidate for having an ammonia-associated disease or disorder or phenylketonuria; or (iii) is undergoing an anti-hyperammonemia or an anti-phenylketonuria treatment.

Item 27. A method of using the polymersome defined in any one of items 1 to 14 and 17, the composition of any one of items 19 to 21 or the strip of item 22, for determining the concentration of ammonia in a sample, comprising:
(a) contacting the polymersome, composition or strip with the sample;
(b) determining at least one pH-dependent spectroscopic property in the polymersome- or composition-containing sample or the sample-containing strip; and
(c) determining the ammonia concentration in the sample using the at least one pH-dependent spectroscopic property by referring to a standard curve.

Item 28. The method of item 27, wherein the pH-dependent spectroscopic property is a pH-dependent absorbance, the pH-sensitive dye is a pH-dependent absorbance dye and the standard curve is an absorbance standard curve.

Item 29. The method of item 27, wherein the pH-dependent spectroscopic property is a pH-dependent fluorescence intensity, the pH-sensitive dye is a pH-sensitive fluorescent dye and the standard curve is a fluorescence standard curve.

Item 30. The method of item 27, wherein (b) further comprises determining at least one pH-independent spectroscopic property or at least one further pH-dependent spectroscopic property in the polymersome- or composition-containing sample or the sample-containing strip to calculate at least one spectroscopic property ratio, and wherein (c) determines the ammonia concentration in the polymersome- or composition-containing sample or the sample-containing strip using the at least one pH-dependent spectroscopic property ratio by referring to a spectroscopic property ratio standard curve.

Item 31. The method of item 30, wherein the at least one pH-dependent spectroscopic property and the at least one pH-independent spectroscopic property are produced by the same pH-sensitive dye.

Item 32. The method of item 30 or 31, wherein the spectroscopic property is absorbance, and the pH-sensitive dye is a pH-sensitive absorbance dye.

Item 33. The method of item 30 or 31, wherein the spectroscopic property is fluorescence, and the pH-sensitive dye is a pH-sensitive fluorescent dye.

Item 34. The method of any one of items 27 to 33, wherein the pH within the polymersome core is between 2 and 6.5.

Item 35. The method of any one of items 27 to 34, wherein the at least one pH-sensitive dye comprises a hydroxypyrene or one of its derivatives.

Item 36. The method of item 35, wherein the at least one pH-sensitive dye comprises 8-hydroxypyrene-1,3,6-trisulfonate (HPTS).

Item 37. The method of any one of items 27 to 34, wherein the at least one pH-sensitive dye comprises a pyridylphenyloxazole or one of its derivatives; an aminonaphthalene or one of its derivatives; or cyanine or one of its derivatives.

Item 38. The method of item 37, wherein the at least one pH-sensitive dye comprises dextran-conjugated Lysosensor™ Yellow/Blue, ANTS or IRDye™ 680RD carboxylate.

Item 39. The method of any one of items 27 to 38, wherein the sample comprises a body fluid sample from a subject.

Item 40. The method of item 39, wherein the body fluid is a blood or blood fraction sample, a saliva sample, or a semen sample.

Item 41. The method of item 40, wherein the body fluid has been pretreated with phenylalanine ammonia lyase.

Item 42. The method of item 40 or 41, which is for (i) diagnosing an ammonia-associated disease or disorder or phenylketonuria in the subject, wherein an ammonia concentration in the sample that is higher than a reference ammonia concentration is an indication that the subject has an ammonia-associated disease or disorder or phenylketonuria; or for (ii) monitoring the efficiency of an anti-hyperammonemia or an anti-phenylketonuria treatment, wherein an ammonia concentration in the sample that is lower than a reference ammonia concentration is an indication that the anti-hyperammonemia or anti-phenylketonuria treatment is effective.

Item 43. A kit for determining the concentration of ammonia in a sample comprising (a) the polymersome defined in any one of items 1 to 14 and 17, the composition defined in any one of items 19 to 21 or the strip of item 22, and (b) (i) a solution for hydrating the polymersome; (ii) a buffer for adjusting the pH of the outer phase of the polymersome and/or the sample to be assayed; (iii) a diluent for diluting the sample to be assayed; (iv) a fluorescence standard curve and/or an absorbance standard curve; (v) one or multiple solutions of known ammonia concentration; or (vi) a combination of at least two of (i) to (v).

Other objects, advantages and features of the present invention will become more apparent upon reading of the following non-restrictive description of specific embodiments thereof, given by way of example only with reference to the accompanying drawings.

DESCRIPTION OF ILLUSTRATIVE EMBODIMENTS

Figure 1:
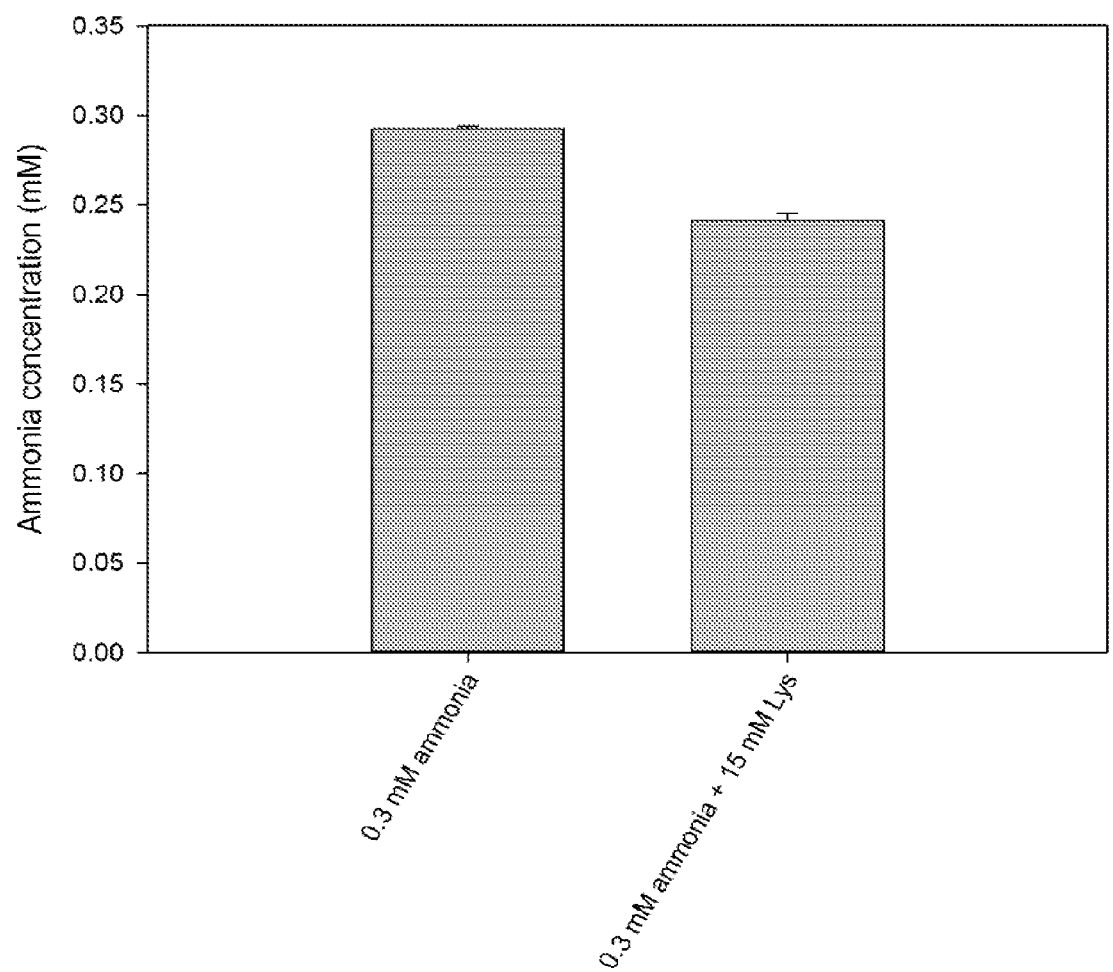
FIG. 1 shows the effect of L-lysine on Berthelot reaction-based ammonia quantification. The presence of L-lysine leads to an underestimation of the ammonia concentration using the Berthelot reaction. Results expressed as mean and standard deviation (n=3).

The present invention encompasses transmembrane pH-gradient polymersomes to quantify ammonia in body fluids, compositions comprising the polymersomes, processes for making the polymersomes and the use of these polymersomes and compositions.

Polymersomes

Polymersomes are vesicles, the bilayer membrane of which is assembled from synthetic copolymers. They have mean diameters ranging from 50 nm to 100 µm or more, in a specific embodiment, ranging from 100 nm to 40 µm, as determined by laser diffraction. Although tested polymersomes of the present invention having mean diameters varying between 100 nm to 40 µm were able to effectively encapsulate ammonia, there is no reason to believe that polymersomes with a diameter larger than 40 µm could not also be effective.

Polymersomes of the present invention comprise amphiphilic block copolymers and are prepared using an organic solvent.

The mechanism of action of the present invention is based on the pH gradient across the polymersome membrane. The acidic agent contained in the aqueous polymersome core possesses a pH different (lower than) from the sample pH (e.g., physiological pH), or sample pH after addition of buffer, in various fluid samples (e.g., body fluid samples) used for the present invention. Typically, human blood and its liquid fractions have a pH between 7.35 and 7.45; saliva has a pH between 6.7 and 7.4 (Baliga et al J Indian Soc Periodontol. 2013; 17:461-465); urine has a pH between 4.5 and 7.5 (Maalouf et al. Clinical Journal of the American Society of Nephrology 2007; 2:883-888); sweat has a pH between 4.5 and 7 (Oncescu et al. Lab Chip 2013; 13:3232-3238); and semen has a pH between 7.2 and 8.0 (Haugen et al. International Journal of Andrology 1998; 21:105-108). Such ranges are similar in other mammals. Hence, ammonia can diffuse through the hydrophobic polymeric membrane of the polymersomes in their uncharged state and be then trapped in their protonated (ionized) state (e.g., ammonium in the case of ammonia) in the inner compartment. While ammonia is mainly existing in its protonated state at the pH of the samples (e.g., body fluids), used as is or diluted with a buffer, there is always a small fraction of ammonia in its non-ionized state. This fraction can diffuse in the polymersomes and be trapped in its protonated state inside the polymersomes. The protonation of the ammonia molecule consumes a proton which increases the pH inside the polymersome core. The ammonia/ammonium equilibrium is quickly reestablished in the outer phase (i.e., ammonium deprotonation to reestablish the ammonia fraction), yielding further ammonia molecules which can diffuse into the polymersome core. The spectroscopic property (fluorescence intensity or absorbance) at a pH-dependent wavelength of the pH-sensitive dye inside the polymersome core changes with the ammonia concentration increase in the core.

As used herein the property "transmembrane pH gradient to quantify ammonia" refers to the ability of the polymersomes of the present invention to sequester ammonia when diluted in a sample (e.g., body fluid sample) (which may itself have been diluted in a buffer).

Block Copolymers

"Polymers" are macromolecules comprising connected monomeric units. The monomeric units may be of a single type (homopolymer), or a variety of types (copolymer). A copolymer made of a sequence of two or more monomers of a single type (a block) covalently joined to two or more monomers of another type (another block) is called a block copolymer. A copolymer made of two block types covalently joined together is called a diblock, of three block types, is called a triblock, etc. Block copolymers can comprise, as a result of the specific synthesis used to generate them, different end groups.

Polymersomes of the present invention comprise block copolymers. In a specific embodiment, the block copolymers of the present invention are diblock or triblock copolymers. These block copolymers are amphiphilic and are formed of at least two polymers, namely an aromatic highly hydrophobic polymer (e.g. poly(styrene)) and a hydrophilic uncharged and non-biodegradable polymer. In a more specific embodiment, the block copolymer is a diblock copolymer (e.g., poly(styrene)-b-poly(ethylene oxide) (PS-b-PEO)), or a triblock copolymer (e.g., PEO-b-PS-b-PEO)) (i.e. PS PEO block copolymers)).

An "amphiphilic" copolymer is one containing both hydrophilic: (water-soluble) and hydrophobic (water-insoluble) groups.

As used herein the term "non-biodegradable" means non-hydrolysable in fluid samples conditions (e.g., body fluid sample) (e.g., resistant to degradation through pH, enzymes, or other means).

Hydrophobic Uncharged Polymer

In a specific embodiment, the hydrophobic uncharged polymer used in copolymers of the present invention is a poly(ethylethylene) ($-(CH_2-CH(C_2H_5))_n-$, i.e. $-(C_4H_8)_n-$) or a poly(styrene) ($-(CH_2-CH(Ph))_n-$, i.e. $-(CH_2-CH(C_6H_5))_n-$, or $-(C_8H_8)_n-$). In specific embodiments, the hydrophobic uncharged polymer is a poly(styrene) (PS). Poly(styrenes) for use in the present invention may include non-substituted and/or substituted/functionalized styrene monomers. Unless specifically defined otherwise, the term "poly(styrene)" is therefore used herein generically to designate a poly(styrene) that comprises exclusively non-substituted styrene monomers, a mix of substituted and non-substituted styrene monomers or exclusively substituted styrene monomers. The one or more substituents on the styrene monomer may include substituents on the phenyl and/or on the carbon on which the phenyl is attached and/or may form polycyclic derivatives with the phenyl (e.g., bicycles, tricycles, etc. comprising C3-C6 aryl(s) and/or C3-C6 cycloalkyl(s)). Potential substituents include alkyl (C1 to C7 (C1, C2, C3, C4, C5, C6 or C7, more specifically C1, C2 or C3), aryl (C3-C6), C3-C8 cycloalkyl, aryl-alkyl, acetoxyl, alkoxyl (methoxyl, ethoxyl, propanoxyl, butoxyl, etc.), halogen (Br, Cl, F, etc.), amine, amide, alkylamine, $NO_2$. The substituents may themselves be substituted. Without being so limited, the substituted styrene monomer include acetoxystyrene, benshydrylstyrene, benzyloxy-methoxystyrene, bromostyrene (2-, 3-, 4- or alpha), chlorostyrene (2-, 3-, 4- or alpha), fluorostyrene (2-, 3-, 4- or alpha), tert-butoxystyrene, tert-butylstyrene, chloro-methylstyrene, diclhlorostyrene, diflurostyrene, dimethoxystyrene, dimethylstyrene, dimethylvinylbenzylamine, diphenyl methyl pentene, (diphenylphosphino)styrene, ethoxystyrene, isopropenyl aniline, isopropenyl-α,α-dimethylbenzyl isocyanate, [N-(methylaminoethyl)aminomethyl]styrene, methylstyrene, nitrostyrene, pentafluorophenyl 4-vinylbenzoate, pentafluorstyrne, (trifluormethyl)styrene (2-, 3-, or 4-), trimethylstyrene, vinylaniline (3-, or 4-), vinylanisole, vinylbenzoic acid (3-, 4-), vinylbenzyl chloride, (vinylbenzyl)trimethylammonium vinylbiphenyl, 4-vinylbenzocyclobutene (4-, etc.), vinylanthracene (9-, etc.), 2-vinylnaphthalene, vinyl-biphenyl (3-, 4-, etc.), etc. In an embodiment, the PS comprises at least one substituted styrene monomer. The substituents may be non-ionic groups (e.g., methyl- or tert-butyl groups). In particular embodiments, the substituted styrene monomer is an alkylstyrene (e.g., methyl styrene) or a tert-butylstyrene. In another specific embodiment, the styrene monomers in the poly(styrene) are unsubstituted.

Hydrophilic Uncharged Polymer

Hydrophilic uncharged polymer that can be used with poly(styrene) in the block copolymer of the present invention include poly(ethylene oxide), poly(vinyl pyrrolidone), poly(ethyl oxazoline), poly(methyl oxazoline), and polymers of oligoethylene glycol alkyl acrylate. In specific embodiments, the hydrophilic uncharged polymer is poly (ethylene oxide).

Poly(ethylene oxide) (PEO) for use in the present invention has the general formula: ($-(O-CH_2-CH_2)_n-$, i.e. $-(C_2H_4O)_n-$) and includes non-substituted and substituted/functionalized ethylene oxide monomers. Unless specifically defined otherwise, the term "poly(ethylene oxide)" or PEO is therefore used herein generically to designate a PEO that comprises exclusively non-substituted ethylene oxide monomers, a mix of substituted and non-substituted ethylene oxide monomers or exclusively substituted ethylene oxide monomers. In an embodiment, the PEO comprises at least one substituted ethylene oxide monomer. In another embodiment, the ethylene oxide monomers are unsubstituted.

Polymers⊖ Proportion

The molecular weights of the PS and PEO blocks (e.g., diblock PS-b-PEO or triblock PEO-b-PS-b-PEO) can be varied as long as the structure and stability of the bilayer is preserved. The inventors found that stable PS-b-PEO polymersomes form between a PS/PEO number average molecular weight ratio higher than 1.0 and lower than 4 (see e.g., Ex. 2-16). In a specific embodiment, the ratio is about 1.1 or higher and lower than 4. In another specific embodiment, the ratio is about 1.2 or higher and lower than 4. In another specific embodiment, the ratio is about 1.3 or higher and lower than 4. In another specific embodiment, the ratio is about 1.4 or higher and lower than 4. In another specific embodiment, the ratio is higher than 1 and about 3.9 or lower. In a specific embodiment, the ratio is about 1.1 or higher and lower than 3.9. In another specific embodiment, the ratio is about 1.2 or higher and lower than 3.9. In another specific embodiment, the ratio is about 1.3 or higher and lower than 3.9. In another specific embodiment, the ratio is about 1.4 or higher and lower than 3.9. In another specific embodiment, the ratio is higher than 1 and about 3.8 or lower. In a specific embodiment, the ratio is about 1.1 or higher and lower than 3.8. In another specific embodiment, the ratio is about 1.2 or higher and lower than 3.8. In another specific embodiment, the ratio is about 1.3 or higher and lower than 3.8. In another specific embodiment, the ratio is about 1.4 or higher and lower than 3.8. In another specific embodiment, the ratio is higher than 1 and about 3.7 or lower. In a specific embodiment, the ratio is about 1.1 or higher and lower than 3.7. In another specific embodiment, the ratio is about 1.2 or higher and lower than 3.7. In another specific embodiment, the ratio is about 1.3 or higher and lower than 3.7. In another specific embodiment, the ratio is about 1.4 or higher and lower than 3.7. In another specific embodiment, the ratio is higher than 1 and about 3.6 or lower. In a specific embodiment, the ratio is about 1.1 or higher and lower than 3.6. In another specific embodiment, the ratio is about 1.2 or higher and lower than 3.6. In another specific embodiment, the ratio is about 1.3 or higher and lower than 3.6. In another specific embodiment, the ratio is about 1.4 or higher and lower than 3.6. In another specific embodiment, the ratio is higher than 1 and about 3.5 or lower. In a specific embodiment, the ratio is about 1.1 or higher and lower than 3.5. In another specific embodiment, the ratio is about 1.2 or higher and lower than 3.5. In another specific embodiment, the ratio is about 1.3 or higher and lower than 3.5. In another specific embodiment, the ratio is about 1.4 or higher and lower than 3.5. In another specific embodiment, the ratio is higher than 1 and about 3.4 or lower. In a specific embodiment, the ratio is about 1.1 or higher and lower than 3.4. In another specific embodiment, the ratio is about 1.2 or higher and lower than 3.4. In another specific embodiment, the ratio is about 1.3 or higher and lower than 3.4. In another specific embodiment, the ratio is about 1.4 or higher and lower than 3.4. In another specific embodiment, the ratio is higher than 1 and about 3.3 or lower. In a specific embodiment, the ratio is about 1.1 or higher and lower than 3.3. In another specific embodiment, the ratio is about 1.2 or higher and lower than 3.3. In another specific embodiment, the ratio is about 1.3 or higher and lower than 3.3. In another specific embodiment, the ratio is about 1.4 or higher and lower than 3.3. In another specific embodiment, the ratio is higher than 1 and about 3.2 or lower. In a specific embodiment, the ratio is about 1.1 or higher and lower than 3.2. In another specific embodiment, the ratio is about 1.2 or higher and lower than 3.2. In another specific embodiment, the ratio is about 1.3 or higher and lower than 3.2. In another specific embodiment, the ratio is about 1.4 or higher and lower than 3.2. In another specific embodiment, the ratio is higher than 1 and about 3.2 or lower. In a specific embodiment, the ratio is about 1.1 or higher and lower than 3.1. In another specific embodiment, the ratio is about 1.2 or higher and lower than 3.1. In another specific embodiment, the ratio is about 1.3 or higher and lower than 3.1. In another specific embodiment, the ratio is about 1.4 or higher and lower than 3.1. In a specific embodiment, the ratio is about 1.1 or higher and lower than 3. In another specific embodiment, the ratio is about 1.2 or higher and lower than 3. In another specific embodiment, the ratio is about 1.3 or higher and lower than 3. In another specific embodiment, the ratio is about 1.4 or higher and lower than 3. In another specific embodiment, the ratio is higher than 1 and about 2.9 or lower. In another specific embodiment, the ratio is about 1.1 or higher and about 2.9 or lower. In another specific embodiment, the ratio is about 1.2 or higher and about 2.9 or lower. In another specific embodiment, the ratio is about 1.3 or higher and about 2.9 or lower. In another specific embodiment, the ratio is about 1.4 or higher and about 2.9 or lower. In another specific embodiment, the ratio is higher than 1 and about 2.8 or lower. In another specific embodiment, the ratio is about 1.1 or higher and about 2.8 or lower. In another specific embodiment, the ratio is about 1.2 or higher and about 2.8 or lower. In another specific embodiment, the ratio is about 1.3 or higher and about 2.8 or lower. In another specific embodiment, the ratio is about 1.4 or higher and about 2.8 or lower. In another specific embodiment, the ratio is higher than 1 and about 2.7 or lower. In another specific embodiment, the ratio is higher than about 1.1 and about 2.7 or lower. In a specific embodiment, the ratio is between about 1.2 and about 2.7 or lower. In a specific embodiment, the ratio is about 1.3 or higher and about 2.7 or lower. In a specific embodiment, the ratio is about 1.4 or higher and about 2.7 or lower. In another specific embodiment, the ratio is higher than 1 and about 2.6 or lower. In another specific embodiment, the ratio is higher than about 1.1 and about 2.6 or lower. In a specific embodiment, the ratio is between about 1.2 and about 2.6 or lower. In a specific embodiment, the ratio is about 1.3 or higher and about 2.6 or lower. In a specific embodiment, the ratio is about 1.4 or higher and about 2.6 or lower. In another specific embodiment, the ratio is higher than 1 and about 2.5 or lower. In another specific embodiment, the ratio is higher than about 1.1 and about 2.5 or lower. In a specific embodiment, the ratio is between about 1.2 and about 2.5 or lower. In a specific embodiment, the ratio is about 1.3 or higher and about 2.5 or lower. In a specific embodiment, the ratio is about 1.4 or higher and about 2.5 or lower. In another specific embodiment, the ratio is higher than 1 and about 2.4 or lower. In another specific embodiment, the ratio is higher than about 1.1 and about 2.4 or lower. In a specific embodiment, the ratio is between about 1.2 and about 2.4 or lower. In a specific embodiment, the ratio is about 1.3 or higher and about 2.4 or lower. In a specific embodiment, the ratio is about 1.4 or higher and about 2.4 or lower. In another specific embodiment, the ratio is higher than 1 and about 2.3 or lower. In another specific embodiment, the ratio is higher than about 1.1 and about 2.3 or lower. In a specific embodiment, the ratio is between about 1.2 and about 2.3 or lower. In a specific embodiment, the ratio is about 1.3 or higher and about 2.3 or lower. In a specific embodiment, the ratio is about 1.4 or higher and about 2.3 or lower. In another specific embodiment, the ratio is higher than 1 and about 2.2 or lower. In another specific embodiment, the ratio is higher than about 1.1 and about 2.2 or lower. In a specific embodiment, the ratio is between about 1.2 and about 2.2 or lower. In a specific embodiment, the ratio is about 1.3 or higher and about 2.2 or lower. In a specific embodiment, the ratio is about 1.4 or higher and about 2.2 or lower. In another specific embodiment, the ratio is higher than 1 and about 2.1 or lower. In another specific embodiment, the ratio is higher than about 1.1 and about 2.1 or lower. In a specific embodiment, the ratio is between about 1.2 and about 2.1 or lower. In a specific embodiment, the ratio is about 1.3 or higher and about 2.1 or lower. In a specific embodiment, the ratio is about 1.4 or higher and about 2.1 or lower. In another specific embodiment, the ratio is higher than 1 and about 2.0 or lower. In another specific embodiment, the ratio is higher than about 1.1 and about 2.0 or lower. In a specific embodiment, the ratio is between about 1.2 and about 2.0 or lower. In a specific embodiment, the ratio is about 1.3 or higher and about 2.0 or lower. In a specific embodiment, the ratio is about 1.4 or higher and about 2.0 or lower.

Without limiting the generality of the above statements, PEOs having a molecular weight of between about 400 g/mol up to 20,000 g/mol are encompassed by the present invention. However, Applicants have no reason to expect that higher molecular weight PEO could not be effectively used in the present inventions. Polymers of smaller molecular weight may be easier to manipulate. Typically, the PEO molecular weight is between 1000 and 5000 g/mol. The PS molecular weight is selected to satisfy the above described ratio. In accordance with the present invention, when the PEO has a molecular weight of about e.g., 20,000 g/mol, the PS molecular weight is lower than about 80,000 g/mol.

Properties of Polymersomes Made of Hydrophobic Uncharged Polymer+Hydrophilic Uncharged Polymer (Di- or Triblock Copolymers (e.g., PS-b-PEO or PEO-b-PS-b-PEO Copolymers))

Without being limited by this hypothesis, it is believed that the strong interaction of the highly hydrophobic polymer (e.g., aromatic (e.g., PS) with the capacity to make pi stacking interactions) in the vesicle membrane provides resistance against fluid samples (e.g., body fluid samples such as serum, plasma and saliva) and provides selectivity to ammonia (i.e., selective permeability to ammonia and poor permeability to most other biological compounds) as demonstrated by the retained ammonia quantification capacity of transmembrane pH-gradient PS-b-PEO polymersomes in different complex biological environments and in the excess of the primary amine L-lysine (see Ex. 3-9). In specific embodiments, the polymer blocks in the polymersome are non-biodegradable.

Method of Preparation of Polymersomes
Preparation of Copolymer

Any known method for making copolymers can be used. Copolymers used in the Examples described herein were purchased from Advanced Polymer Materials Inc (Dorval, Canada) (PS-b-PEO) (see Ex. 2-11, 14) or synthetized (see Ex. 12-16).

Preparation of Polymersomes

The copolymer is dissolved in an organic solvent to form an organic phase, and the latter is mixed with the aqueous acidic solution (e.g., pH-sensitive dye, and optionally, if the concentration of the pH-sensitive dye is not sufficiently high, a further acid e.g., citric acid) (aqueous phase). The mixing step may be performed through different techniques. For instance, an oil-in-water (o/w) emulsion (i.e. polymer-containing organic solvent phase (i.e. oil phase) in acidic aqueous solution (i.e. water phase)), a reverse-phase evaporation, a nanoprecipitation, or a double emulsion method, may be used to mix the polymer-containing organic phase and the aqueous phase.

As used herein, the term "pH-sensitive dye" refers herein to a dye whose spectroscopic properties depend on the pH of the medium. In particular, it encompasses a pH-sensitive absorbance dye and a pH-sensitive fluorescent dye. As the method of the present invention is based on measuring pH changes in the polymersome core, all pH-sensitive dyes are encompassed by the present invention.

As used herein, the term "absorbance dye" refers to a dye which absorbs certain ultraviolet, visible and/or near infrared wavelengths when irradiated by them. As used herein, the term "pH-sensitive absorbance dye" refers herein to a dye whose absorbance spectrum varies as a function of the pH in the medium. Without being so limited, pH-sensitive absorbance dyes of the present invention include HPTS or a salt thereof (e.g., HPTS potassium or trisodium salt), triarylmethane dyes (e.g., bromocresol green, bromocresol purple, cresol red, chlorophenol red, phenol red, phenolphthalein, malachite green, thymol blue, bromothymol blue), azo dyes (e.g., methyl orange, methyl red, eriochrome black T, congo red), nitrophenol dyes (e.g., 2,4-dinitrophenol), anthraquinone dyes (e.g., alizarin), and the dyes listed under "pH-sensitive fluorescent dye" below.

The pH-sensitive absorbance dye may further comprise at least one pH-independent (isosbestic) wavelength, whose absorbance value is pH-independent and may be used to normalize the absorbance value at the pH-dependent wavelength. The pH-sensitive absorbance dye may further be normalized to an absorbance value at another pH-dependent wavelength (see Ex. 16).

As used herein, the terms "fluorescent dye" refers to a dye which, when irradiated at certain ultraviolet, visible and/or near infrared wavelength, generates a fluorescence intensity that produces a or alters the fluorescence intensity of the solution in which the dye is dissolved at an appropriate concentration. As used herein, the term "pH-sensitive fluorescent dye" refers to a fluorescent dye comprising at least one pH-dependent (excitation or emission) wavelength.

The pH-sensitive fluorescent dye may further comprise at least one pH-independent (isosbestic) (excitation or emission) wavelength, whose fluorescence intensity is pH-independent and may be used to normalize the fluorescence intensity at the pH-dependent (excitation or emission) wavelength. Without being so limited, pH-sensitive fluorescent dyes of the present invention include hydroxypyrene and its derivatives such as HPTS or a salt thereof (e.g., HPTS tripotassium or trisodium salt), phenylpyridyloxazole and its derivatives such as dextran-conjugated Lysosensor™ Yellow/Blue, naphthalene derivatives (e.g., aminonaphthalene and its derivatives such as ANTS or a salt thereof (e.g., disodium or dipotassium salt), cyanine and its derivatives such as IRDye™ 680RD, xanthene derivatives (e.g., fluorescein and its derivatives (e.g., sodium carboxyfluorescein), rhodamine B and its derivatives), coumarin derivatives, squaraine derivatives, oxadiazole derivatives, anthracene derivatives, pyrene derivatives, oxazine derivatives, acridine derivatives, acridine derivatives, arylmethine derivatives, indolinium derivatives ((E)-6-hydroxy-5-sulfo-4-(2-(1,3,3-trimethyl-3H-indol-1-ium-2-yl)vinyl)-2,3-dihydro-1H-xanthene-7-sulfonate, (E)-2-(2-(6-hydroxy-7-(morpholinomethyl)-2,4a-dihydro-1H-xanthen-3-yl)vinyl)-3,3-dimethyl-1-propyl-3H-indol-1-ium iodide, (E)-2-(2-(7-(benzo[d]thiazol-2-yl)-6-hydroxy-2,3-dihydro-1H-xanthen-4-yl)vinyl)-3,3-dimethyl-1-(3-sulfonatopropyl)-3H-indol-1-ium-5-sulfonate), and tetrapyrrole derivatives. Of note, near infrared (NIR) fluorescent dyes such as IRDye™ 680RD can be used directly to assay cell containing body fluid samples, such as blood (i.e. whole blood) (i.e., the cells (e.g., erythrocytes) do not need to be removed from the fluid sample prior to the fluorescence assay). Each dye has a specific pH-dependent fluorescence (excitation or emission) intensity profile: the polymersome core pH is adapted to the pH range wherein the dye is most sensitive to pH changes (i.e., wherein the fluorescence (excitation or emission) intensity spectrum of the dye shows the strongest pH dependency). In a specific embodiment, the pH in the polymer core is between about 2 and 6.5. In a more specific embodiment, the pH in the polymer core is about between 2 and 5.5.

More than one dye can be used. For example, but without being so limited, a pH-sensitive fluorescent dye which comprises at least one pH-dependent wavelength, but no pH-independent wavelength may be combined with another dye which comprises at least one pH-independent wavelength (e.g., for calibration purposes).

The concentration of the pH-sensitive dye in the polymersome core is selected so as to generate an appropriate absorbance or fluorescence intensity. In the absence of another acid, the pH of the polymersome core and concentration of the pH-sensitive acidic dye (e.g., fluorescent) are selected to display a progressive alteration in the pH-dependent fluorescence intensity in relation to the concentration of ammonia in the polymersome core. The concentration of the pH-sensitive dye typically ranges from about 0.002 to about 200 mM. In a specific embodiment, when a pH-sensitive fluorescent dye is used, the range is from about 0.002 to about 200 mM. In examples disclosed herein, it ranges from about approx. 0.01 mM (LysoSensor™ Yellow/Blue dextran, 10,000 MW) to about 10 mM (pyranine and ANTS). In the oil-in-water (o/w) emulsion method, the polymer-containing organic solvent is mixed with the aqueous acidic phase (containing the pH-sensitive dye) under sonication for a time sufficient to form an emulsion. In the examples below, the aqueous phase was saturated with organic solvent under stirring for 30 minutes prior to the addition of the polymer-containing organic solvent phase. Subsequently, the polymer-containing organic solvent phase was added to the acid-containing aqueous phase under sonication in an ice bath (to reduce the heat produced by the sonicator), using the following machine-specific parameters: amplitude 70, cycle 0.75 (UP200H, 200 W, 24 kHz, Hielscher Ultrasound Technology with sonotrode S1) for 3 min or amplitude 10 (3.1 mm sonotrode, Fisher Scientific Model 705 Sonic Dismembrator™, 700 W, 50/60 Hz, Fisher Scientific) for 2 min. Any method known in the art to create an emulsion may be used. The use of sonication as well as the specific sonication parameters and time appropriate for producing an emulsion will depend on the emulsion technique used. The emulsion does not need to be stable in the methods of preparation of the present invention.

In the reverse-phase evaporation method, a two-phase system comprising of a polymer-containing organic solvent and a pH-sensitive dye, and, if appropriate, an additional acid-containing aqueous phase is sonicated, forming a water-in-oil (w/o) emulsion. The outer phase is evaporated under reduced pressure until a viscous gel-like state is formed. Polymersomes form upon the collapse of the gel state (Krack et al. J. Am. Chem. Soc. 2008; 130:7315-7320). The solvent and unencapsulated dye are subsequently removed.

In the nanoprecipitation method, the polymers are dissolved in a suitable organic solvent, to which a pH-sensitive dye- and, if appropriate, an additional acid-containing water is slowly added. Alternatively, the organic phase could be added to the aqueous phase. The solvent and unencapsulated dye are subsequently removed.

In the double-emulsion method, polymersomes form in a w/o/w double emulsion containing a pH-sensitive dye- and, if appropriate, an additional acid-containing aqueous inner phase, a polymer-containing completely or partially water immiscible organic solvent in the middle phase, and an aqueous outer phase. The solvent and unencapsulated dye are subsequently removed.

The pH (e.g., neutral and basic pH) and the composition (without buffer (i.e., dilution of the polymersome-containing solution in naturally buffered physiological solutions such as serum or plasma) or with buffer) in the outer/external phase may also be varied. Increasing the pH of the outer phase promises to accelerate the uptake kinetics to even higher velocities because of the increased fraction of ammonia in the equilibrium ammonia/ammonium.

As used herein, the "buffer" for use in the polymersome outer/external phase and/or added in body fluid samples to be assayed is used to stabilize the pH or to increase it in order to further deprotonate ammonium in the sample to be assayed (i.e. increase ammonia abundance) and thereby increase diffusion rate of ammonia in polymersomes. It is expected that any neutral or alkaline buffer is appropriate for the stabilization of the pH and any alkaline buffer is appropriate for the increase of the pH. Without being so limited, it may more particularly be a buffer containing phosphate, borate, 4-(2-hydroxyethyl)-1-piperazineethanesulfonic acid (HEPES), 3-(N-morpholino)propanesulfonic acid (MOPS), imidazole, hydrogencarbonate and carbonate salts, or tris (hydroxymethyl)aminomethane.

The buffer concentration in the outer phase or added to the sample (e.g., body fluid) to be tested is selected so as to ensure an appropriate pH value of the resultant solution to create a sufficient pH gradient, in view of the polymersome core pH, which is dependent on the dye's pH profile. It typically ranges from about 2 to about 150 mM. In a specific embodiment, it is about 2 to about 60 mM, or about 4 to about 50 mM.

The pH of the buffer in the outer phase or of the buffer added to the sample (e.g., body fluid) to be tested is selected so as to provide a sufficient pH gradient between the outer and the inner phase and to ensure an appropriate kinetics profile. It typically ranges from pH 7-10. In a specific embodiment, it is about pH 7.4 (i.e., the pH of the PBS buffer used to prepare an ammonia standard curve) (see Ex. 2-16). In another specific embodiment, the pH of all samples to be assayed is adjusted to be the same pH value as the ammonia or phenylalanine standards to enable comparisons (see Ex. 2-16). In yet another specific embodiment, after addition of the polymersome with a buffered exterior phase at pH 7.4 to the phenylalanine samples to be assayed at pH 8.5 and to the phenylalanine standard curve at pH 8.5, the resulting pH of the dispersion also around 7.4 (see Ex. 15). However, the pH of the sample to be tested and the standards do not have to be identical if the pH is adjusted upon mixing the standard or the sample with the polymersome dispersion, whereas the buffering capacity of the outer phase in the polymersome dispersion would set the pH, and/or with an additional buffer setting the pH of the resultant dispersion. In a specific embodiment, the pH of the outer phase of the dispersion resulting from mixing the polymersome dispersion with the sample to be assayed and, if appropriate, an additional buffer, is adjusted to be the same pH as the one in the outer phase of the dispersion resulting from mixing the polymersome dispersion with the ammonia or phenylalanine standards and, if appropriate, an additional buffer, to enable comparisons. Without being so limited, a pH of 7.4 to assay blood and blood fraction samples is also advantageous in that, since it corresponds to the pH of such samples, it limits the risk of potential pH-dependent artifacts. If a sufficient pH gradient can be created between the polymersome core and the sample to be assayed, by the inherent buffering capacity of the sample, any buffer externally added to the exterior phase can be omitted.

As used herein, the term "sufficient gradient" is generally understood to be a difference of at least one pH unit, and in a preferred embodiment, at least 1 pH unit, preferably at least 2 pH units, between the core pH and the sample to be assayed (e.g., a pH of 6 or more in the sample and a pH of 5 or less in the core, preferably a pH of 7 or more in the sample and a pH of 5 or less in the core). Typically, samples to be assayed inherently have or are adjusted (through the addition of a buffer directly or through the addition of polymersomes with a buffered outer phase) to have a pH of about 7 to about 10.

The organic solvent used in the preparation process is removed from the polymersome using any known technique. Without being so limited an application of lower than ambient pressure, heat, filtration, cross-flow filtration, dialysis, or a combination of these methods may be used to remove the solvent.

After elimination of the organic solvent, the polymersomes are purified to decrease the amount of unencapsulated pH-sensitive dye and, if desired, to adapt the pH of the outer phase. The unencapsulated pH-sensitive dye is removed from the polymersome dispersion using any known technique. Without being so limited, (cross-flow) filtration, centrifugation (e.g., centrifugal filtration), size-exclusion chromatography (e.g., gel permeation chromatography, gel filtration chromatography), dialysis, or a combination of these methods may be used to remove the unencapsulated pH-sensitive dye.

The purified polymersome dispersion can then be used as is (with aqueous acid solution outside and inside the polymersomes or after exchange of the external acidic solution with a solution at higher pH, e.g., 7 to 10), further dried by conventional pharmaceutical drying procedures (e.g., freeze drying, spray drying), and/or incorporated into a diagnostic strip. In all such forms (as is, purified and/or dried), the polymersome core contains a pH-sensitive dye, and, optionally, e.g., if the dye is not at a concentration required to produce a sufficient pH gradient for the sample to be assayed, the polymersome core further contains an acid. The acid and/or the pH-sensitive dye provides the transmembrane pH gradient to the polymersome when it is mixed with the sample (e.g., body fluid) to be assayed (with or without an additional buffer). The so formed polymersomes of the present invention may further contain salt (i.e., partially deprotonated acid with counterion such as sodium, potassium or calcium), which may be added during the polymersome preparation to adjust the pH and/or osmolarity in the core, and, in their hydrated form, polymersomes further contain water. In specific embodiments, the core may further contain a preservative, which may be added during the polymersome preparation to prevent microbial growth in the core in cases where e.g., the core pH is relatively high (e.g., pH 5.5 or more). After its use in methods of the present invention, the core may further contain ammonia. In accordance with specific embodiments, the polymersomes core content may comprise or consist of at least one pH-sensitive dye. In other embodiments, the core may further comprise at least one acid. In other embodiments, the core may further comprise at least one salt. In other embodiments, the core may further comprise water. In other embodiments, the core may further comprise at least one preservative. In other embodiments, the core may further comprise ammonia. In yet other embodiments, the polymersome core content may consist of (a) at least one pH-sensitive dye; and (b) (i) at least one acid; (ii) at least one salt; (iii) water; (iv) at least one preservative; (v) ammonia; or (vi) a combination of at least two of (i) to (v).

When the polymersomes are hydrated (i.e., containing an aqueous acidic core), the pH in their core is generally between about 1 and 6.5 (1, 1.5, 2, 2.5, 3, 3.5, 4, 4.5, 5, 5.5, 6, or 6.5). In a specific embodiment, it is between about 1 and about 6.5, between about 1 and about 6, between about 1 and about 5.5, between about 1 and about 4.5, between about 1 and about 4, between about 1.5 and about 5, between about 1.5 and about 4.5, between about 1.5 and about 4, between about 2 and about 6.5, between about 2 and about 6, between about 2 and about 5.5, between about 2 and about 5, between about 2 and about 4.5, between about 2 and about 4, between about 2.5 and about 6.5, between about 2.5 and about 6, between about 2.5 and about 5.5, between about 2.5 and about 5, between about 2.5 and about 4.5, between about 2.5 and about 4, between about 3 and about 6.5, between about 3 and about 6, between about 3 and about 5.5, between about 3 and about 5, between about 3 and about 4.5, and between about 3 and about 4.

Although it is not necessary for the stability of the polymersomes of the present invention, the polymersome membrane can also be crosslinked. For instance, a Friedel-Crafts reaction with the crosslinking agent p-xylylene-dichloride, 1,4-bis-chloromethyldiphenyl, monochlorodimethyl ether, dimethylformal, tris-(chloromethyl)-mesitylene, or p,p'-bis-chloromethyl-1,4-diphenylbutane may be used to crosslink poly(styrene) (Davankov and Tsyurupa, Reactive Polymers 1990; 13:27-42).

Solvent

The solvent used in the present invention dissolves the copolymer, and the polymer-containing solvent is then mixed with the acidic aqueous phase. During the mixing step (e.g., o/w emulsion), a fine dispersion of the polymer is formed in the aqueous phase. After the mixing step, the solvent is removed (e.g., evaporated) to ensure that the stability of the polymersomes is maintained (e.g., solvent could potentially plasticize the membrane yielding more permeable polymersomes).

A concentration of about 2% to about 40% (v/v) solvent phase/aqueous phase ratio may be used. In a specific embodiment, the solvent phase/aqueous phase ratio is of about 5% to 30% (v/v). In another specific embodiment, the solvent phase/aqueous phase ratio is of about 5% to 20% (v/v). In another specific embodiment, the solvent phase/aqueous phase ratio is of about 5% to 15% (v/v). In another specific embodiment, the solvent phase/aqueous phase ratio is of about 10% (v/v). In a specific embodiment, the solvent phase/aqueous phase ratio in the resulting emulsion is about 9% (v/v). In specific embodiments, the solvent is an organic solvent.

Without being so limited, the solvent may be a chlorinated solvent (e.g., dichloromethane see e.g., Ex. 2-16 or chloroform), aromatic solvent or aromatic solvent derivatives (e.g., arene or arene derivative such as toluene), aliphatic solvent or aliphatic solvent derivative (e.g., hexane, 1-hexanol), ketone or ketone derivative (e.g., 2-hexanone), ether or ether derivative (e.g., diethyl ether), or mixtures thereof (e.g., when using an o/w emulsion, w/o/w double emulsion or reverse-phase evaporation technique).

In a specific embodiment, when an o/w emulsion is used to mix the polymer-containing organic phase and the aqueous phase, solvents useful for the present invention are water immiscible or partially water immiscible organic solvents. Without being so limited such solvents include e.g., dichloromethane (see e.g., Ex. 2-16), chloroform, aromatic solvent or aromatic solvent derivatives (e.g., arene or arene derivative such as toluene), aliphatic solvent or aliphatic solvent derivative (e.g., hexane, 1-hexanol), ketone or ketone derivative (e.g., 2-hexanone), ether or ether derivative (e.g., diethyl ether), or mixtures thereof.

Acid and Acidic Solution

In specific embodiment, the pH-sensitive dye is the acid that promotes the transmembrane pH-gradient. Weak acid pH-sensitive dyes present in sufficiently high concentration (e.g., pyranine at 10 mM) could be used without an additional acid (see Ex. 13). Without being so limited, the pH-sensitive dye HPTS (e.g., pyranine), for instance, buffers around pH 5.5 (i.e., approx. 1.7 pH units below its pKa of 7.2 (Kano and Fendler BBA Biomembranes 1978; 509:289-299)) which enables ammonia sensing in the absence of a further acid. In specific embodiments, the acid used is not the pH-sensitive dye for optimal ammonia measurements (see Ex. 2-12, 14-16). As used herein, the term "weak acid" refers to weak acids having a pKa value of 3.5 or higher and moderately strong acids having a pKa value of −0.35 or higher (Mortimer and Mueller, Chemie, $12^{nd}$ edition, Thieme, 2015).

Without being so limited, the acid enclosed in the polymersome core is (i) a hydroxy acid such as citric acid, isocitric acid, malic acid, tartaric acid, or lactic acid; (ii) an aliphatic acid such as short-chain fatty acids (e.g., acetic acid) or unsaturated acids (e.g., sorbic acid); (iii) a sugar acid such as uronic add; (iv) a dicarboxylic acid such as malonic acid; (v) a tricarboxylic acid such as propane-1,2,3-tricarboxylic acid or aconitic add; (vi) a tetracarboxylic add such as 1,2,3,4-butanetetracarboxylic acid; (vii) a pentacarboxylic acid such as 1,2,3,4,5-pentanepentacarboxylic acid; (viii) a polymeric poly(carboxylic acid) such as poly(acrylic acid) or poly(methacrylic acid); (ix) a polyaminocarboxylic acid such as ethylenediaminetetraacetic acid; (x) an amino acid such as glutamic add or aspartic add; (xi) an inorganic add such as nitric acid, sulfuric acid, hydrogen halides; (xii) an aromatic carboxylic acid such as benzoic acid; (xiii) an acidic pH-sensitive dye such as but not limited to hydroxypyrene and its derivatives (e.g., pyranine, also called HPTS trisodium salt), phenylpyridyloxazole and its derivatives (e.g., dextran-conjugated Lysosensor™ Yellow/Blue), aminonaphthalene and its derivatives (e.g., ANTS), cyanine and its derivatives (e.g., IRDye™ 680RD), triarylmethane dyes (e.g., bromocresol green, bromocresol purple, cresol red, chlorophenol red, phenol red, phenolphthalein, thymol blue, bromothymol blue), azo dyes (e.g., methyl red, eriochrome black T), nitrophenol dyes (e.g., 2,4-dinitrophenol), anthraquinone dyes (e.g., alizarin); or (xiv) a combination of at least two thereof. In a specific embodiment, citric add is used; in another specific embodiment, HPTS is used. The use of a polymer-conjugated pH-sensitive dye (e.g., dextran-conjugated Lysosensor™ Yellow/Blue, dextran-conjugated fluorescein isothiocyanate, methoxy poly(ethylene oxide)-conjugated fluorescein, dextran-conjugated rhodamin B) could be advantageous to reduce dye leakage after purification. Any water soluble polymer such as but without being so limited, dextran, poly(ethylene oxide), poly(vinyl pyrrolidone), or poly(vinyl alcohol) could then be conjugated to the dye.

Although certain of the above-listed acids may have certain pharmacological activities, at certain doses, the encapsulated acid used in specific embodiments of the polymersome of the present invention is not aimed at exerting a direct pharmacological or imaging function but is solely used to create the transmembrane pH gradient and, where the acid is also the pH-sensitive dye, to sense ammonia-related pH changes in the core. The present invention encompasses the use of any one of the above-cited acids, whether or not they also possess certain pharmacological activities. However, in accordance with certain embodiments or aspects of the present invention, the acid may not be an acid, other than any of the above-listed acids, that is known as an antibiotic, anticancer drug, an antihypertensive drug, an antifungal drug, an anxiolytic drug, an anti-inflammatory drug, an immunomodulatory drug, an antiviral drug, or a lipid lowering agent.

In specific embodiments, the concentration of acid used in the method may be varied between 0.1 and 100 mM and an osmolality of 50 to 700 mOsmol/kg. When citric acid is used, a citric acid solution of between about 0.5 mM and 50 mM at an osmolality of 150-600 mOsmol/kg is optimally used. In another specific embodiment, the osmolality is between 100 and 750 mOsmol/kg. In another specific embodiment, the osmolality is between 100 and 700 mOsmol/kg. In another specific embodiment, the osmolality is between 115 and 700 mOsmol/kg. The acid concentration is selected so as to avoid influencing the assay sensitivity, and, where the acid used is also the pH-sensitive dye, the acid concentration is selected to also enable reliable fluorescence or absorbance measurements:

The acid within the core is present in a concentration that produces a pH between 1 and 6.8, in a more specific embodiment, 1 to 6.5, 2 to 6, when the polymersome is hydrated. In a specific embodiment, a pH of about 5.5 is used. In another specific embodiment, a pH of about 3.0 is used. In yet another specific embodiment, a pH of about 2.0 is used.

Method of Use

The present invention encompasses a method of using the transmembrane pH-gradient polymersomes of the present invention for the quantification of ammonia in various samples. The method may detect ammonia concentration at least as low as about 0.005 mM and at least as high as 8 mM.

In specific embodiments, the precise ammonia concentration in the tested sample can be determined by the following methods.

According to one method, the ammonia concentration in a sample may be assessed by contacting the sample with a polymersome (i.e. containing a pH-sensitive dye) of the present invention (or with a composition or strip containing the polymersome), and measuring at least one pH-dependent spectroscopic property in the polymersome-containing sample, composition-containing sample or sample-containing strip. The ammonia concentration in the sample can then be deduced by comparing the measured spectroscopic property with the spectroscopic property (i.e. absorbance or fluorescence intensity) at the same pH-dependent wavelength in a standard curve of known ammonia concentrations. The standard curve is prepared by first determining a "corresponding reference spectroscopic property" obtained in the specific conditions used in the assay at each specific ammonia concentration. More particularly, the spectroscopic property produced by the same specific pH-sensitive dye at the same specific pH-dependent wavelength, in the core of the same specific transmembrane pH gradient polymersome, with the same specific concentration of acid at the specific pH in the core as those used for assaying a sample with an unknown ammonia amount, if any, is determined in the presence of each specific ammonia concentration outside and inside the polymersome. The "standard curve" is a curve obtained by a mathematical curve fitting procedure to the set of corresponding reference spectroscopic property measured for all tested ammonia concentrations in these conditions. The number of tested ammonia concentrations used to generate the standard curve is at least one (i.e. If the standard curve is linear in the given range, one concentration may be sufficient).

As used herein, the term "spectroscopic property" refers to the absorbance or fluorescence intensity in the electromagnetic spectrum of approx. 10-2000 nm, namely in the ultraviolet (approx. 10-390 nm), the visible (approx. 390-700 nm) and the near infrared (NIR, approx. 700-2000 nm) regions of the spectrum.

As used herein the term "standard curve" is a generic term used to encompass the terms "absorbance standard curve" and "fluorescence standard curve".

Alternatively, a "spectroscopic property ratio" can be determined by normalizing the spectroscopic property of the dye at a pH-dependent wavelength to the spectroscopic property of the same or a different dye at a pH-independent wavelength or at another pH-dependent wavelength. If the dye used does not have a pH-independent wavelength, a second dye having a pH-independent wavelength can be used as reference to calculate the ratio. The spectroscopic property ratio determined on the sample can then be compared to a universal spectroscopic ratio standard curve produced from the universal reference spectroscopic property ratios calculated for each ammonia concentration at the same wavelengths and thus may abrogate the need for a different standard curve obtained for each specific set of assay conditions. Of course, a specific spectroscopic property ratio standard curve produced from the corresponding reference spectroscopic property ratios measured and calculated for the specifically assayed conditions ("specific spectroscopic property ratio standard curve") may still be prepared for optimal precision.

As used herein, the term "universal reference spectroscopic property ratio" refers to the spectroscopic property ratio produced by a pH-sensitive dye at a pH-dependent wavelength and at a pH-independent wavelength (or another pH-dependent wavelength), in the core of a transmembrane pH gradient polymersome, with a certain concentration of acid at a certain pH, in the presence of an ammonia concentration outside and inside the polymersome, in a fluid. The "universal spectroscopic property ratio standard curve" is a curve produced by a mathematical curve fitting procedure to the set of universal reference spectroscopic property ratios calculated in these conditions for all tested ammonia concentrations. The number of tested ammonia concentrations used to generate the standard curve is at least one (i.e. If the standard curve is linear in the given range, one concentration may be sufficient).

As used herein, the term "spectroscopic property ratio standard curve" is a generic term used to encompass the terms "specific spectroscopic property ratio standard curve" and "universal spectroscopic property ratio standard curve". As used herein, the terms "specific spectroscopic property ratio standard curve" and "universal spectroscopic property ratio standard curve" are generic terms used to refer to "specific fluorescence intensity ratio standard curve" and "specific absorbance ratio standard curve"; and "universal fluorescence intensity ratio standard curve" and "universal absorbance ratio standard curve".

As used herein the term "pH-dependent wavelength" and "pH-independent wavelength" are generic terms used to encompass the terms "pH-dependent fluorescence wavelength" and "pH-dependent absorbance wavelength"; and "pH-independent fluorescence wavelength" and "pH-independent absorbance wavelength", respectively.

As used herein the terms "pH-dependent spectroscopic property" and "pH-independent spectroscopic property" are generic terms used to encompass the terms "pH-dependent fluorescence intensity" and "pH-dependent absorbance"; and "pH-independent fluorescence intensity" and "pH-independent absorbance", respectively.

As used herein the term "spectroscopic property ratio" is a generic term used to encompass the terms "fluorescence intensity ratio" and "absorbance ratio".

More specifically, the spectroscopic method above may be a fluorescent or a colorimetric method. Such methods may be as further defined below.

Fluorescence Methods

According to one method, the ammonia concentration in a sample can be deduced by referring to the fluorescence intensity at the same emission and excitation wavelengths in a fluorescence intensity standard curve of known ammonia concentrations. The fluorescence intensity standard curve is prepared by first determining a "corresponding reference fluorescence intensity" obtained in the specific conditions used in the assay at each specific ammonia concentration. More particularly, the fluorescence produced by the same specific pH-sensitive fluorescent dye at the same specific pH-dependent excitation or emission wavelength, in the core of the same specific transmembrane pH gradient polymersome, with the same specific concentration of acid at the specific pH in the core as those used for assaying a sample with an unknown ammonia amount, if any, is determined in the presence of each specific ammonia concentration outside and inside the polymersome. The "fluorescence intensity standard curve" is a curve obtained by a mathematical curve fitting procedure to the set of corresponding reference fluorescence intensities measured for all tested ammonia concentrations in these conditions. The number of tested ammonia concentrations used to generate the standard curve is at least one (i.e. If the standard curve is linear in the given range, one concentration may be sufficient).

Alternatively, a "fluorescence intensity ratio" can be determined by normalizing the fluorescence intensity of the dye at a pH-dependent (emission or excitation) wavelength to the fluorescence intensity of the same or a different dye at a pH-independent (isosbestic) (emission or excitation) wavelength. If the dye used does not have a pH-independent wavelength, a second dye having a pH-independent wavelength can be used as reference to calculate the ratio. The fluorescence intensity ratio determined on the sample can then be compared to a universal fluorescence intensity ratio standard curve produced from the universal reference fluorescence intensity ratios calculated for each ammonia concentration at the same wavelengths and thus may abrogate the need for a different fluorescence intensity standard curve obtained for each specific set of assay conditions. Of course, a specific fluorescence intensity ratio standard curve produced from the corresponding reference fluorescence intensity ratios measured and calculated for the specifically assayed conditions ("specific fluorescence intensity ratio standard curve") may still be prepared for optimal precision.

As used herein, the term "universal reference fluorescence intensity ratio" refers to the fluorescence intensity ratio produced by a pH-sensitive fluorescent dye at a pH-dependent (emission or excitation) wavelength and at a pH-independent (emission or excitation) wavelength, in the core of a transmembrane pH gradient polymersome, with a certain concentration of acid at a certain pH, in the presence of an ammonia concentration outside and inside the polymersome, in a fluid. The "universal fluorescence intensity ratio standard curve" is a curve produced by a mathematical curve fitting procedure to the set of universal reference fluorescence intensity ratios calculated in these conditions for all tested ammonia concentrations. The number of tested ammonia concentrations used to generate the standard curve is at least one (i.e. If the standard curve is linear in the given range, one concentration may be sufficient).

As used herein, the term "fluorescence standard curve" is a generic term used to encompass the terms "fluorescence intensity standard curve" and "fluorescence intensity ratio standard curve". As used herein, the term "fluorescence intensity ratio standard curve" is a generic term used to encompass the term "specific fluorescence intensity ratio standard curve" and "universal fluorescence intensity ratio standard curve".

As used herein, the terms "pH-dependent excitation wavelength" and "pH-independent excitation wavelength" refer to an excitation wavelength whose excitation leads to a pH-dependent fluorescence intensity and a pH-independent fluorescence intensity, respectively, at a certain emission wavelength. As used herein, the terms "pH-dependent emission wavelength" and "pH-independent emission wavelength" refer to an emission wavelength which exhibits a pH-dependent fluorescence intensity and a pH-independent fluorescence intensity, respectively, if excited at a certain excitation wavelength. As used herein, the term "pH-dependent fluorescence wavelength" refers to a pH-dependent emission wavelength or a pH-dependent excitation wavelength. As used herein, the term "pH-independent fluorescence wavelength" refers to a pH-independent emission wavelength or a pH-independent excitation wavelength.

As used herein, the term "pH-dependent fluorescence intensity" refers to a fluorescence intensity generated at either a pH-dependent emission wavelength or a pH-dependent excitation wavelength or to a fluorescence intensity generated at both a pH-dependent emission wavelength and a pH-dependent excitation wavelength. As used herein, the term "pH-independent fluorescence intensity" refers to a fluorescence intensity generated at a pH-independent emission wavelength and a pH-independent excitation wavelength.

Fluorescence intensities are selected either as indicated by the dye supplier or by recording emission and excitation spectra at different pH values and by identifying pH-dependent fluorescence wavelengths and pH-independent fluorescence wavelengths.

Colorimetric Methods

According to another method, the ammonia concentration can be deduced by referring to the absorbance at the same ultraviolet, or visible light or NIR wavelength in an absorbance standard curve of known ammonia concentrations. The absorbance standard curve is prepared by first determining a "corresponding reference absorbance" obtained in the specific conditions used in the assay at each specific ammonia concentration. More particularly, the absorbance of the same specific pH-sensitive absorbance dye at the same specific pH-dependent visible light wavelength, in the core of the same specific transmembrane pH gradient polymersome, with the same specific concentration of acid at the specific pH in the core as those used for assaying a sample with an unknown ammonia amount, if any, is determined in the presence of each specific ammonia concentration outside and inside the polymersome. The "absorbance standard curve" is a curve obtained by a mathematical curve fitting procedure to the set of corresponding reference absorbance values measured for all tested ammonia concentrations in these conditions. The number of tested ammonia concentrations used to generate the standard curve is at least one (i.e. If the standard curve is linear in the given range, one concentration may be sufficient).

As used herein, the term "pH-dependent absorbance wavelength" is used to refer to a wavelength at which the dye absorbs light in the ultraviolet (approx. 10 to 390 nm), visible (approx. 390 to 700 nm) or NIR (approx. 700 to 2000 nm) region of the electromagnetic spectrum, as a function of the pH of the medium. Absorbance wavelengths are selected either as indicated by the dye supplier or by recording absorbance spectra at different pH values and by identifying pH-dependent absorbance wavelengths and pH-independent absorbance wavelengths.

As used herein, the terms "pH-dependent absorbance" and "pH-independent absorbance" refer to an absorbance at a pH-dependent absorbance wavelength and a pH-independent absorbance wavelength, respectively.

Conventional lab-scale or portable spectrophotometers (e.g. standard spectrophotometers for colorimetric methods or fluorescence spectrophotometers for fluorescence methods) and plate readers may be used to measure absorbance or fluorescence in accordance with the present invention.

As used herein the "samples" that can be assayed for ammonia (or indirectly, phenylalanine) content in accordance with the present invention may be, without being so limited, a sample that may contain ammonia or phenylalanine, including a biological sample such as a body fluid sample, soil sample, wastewater sample, or simple buffers. The samples may inherently be fluids or become fluids after addition of an aqueous solution (e.g., soil sample). The samples (inherently fluid or that become fluid after addition of an aqueous solution) may further be modified by optionally adding a buffer and/or enzymes (e.g., for pH stabilization or adjustment and for ammonia-generating enzymatic reactions, respectively). In accordance with specific embodiments, the sample may comprise or consist of a biological sample (e.g., body fluid). In other embodiments, the sample may further comprise an aqueous solution. In other embodiments, the sample may further comprise at least one buffer. In other embodiments, the sample may further comprise at least one enzyme (e.g., phenylalanine ammonia lyase). In yet other embodiments, the sample may consist of (a) a biological sample (e.g., body fluid); and (b) (i) an aqueous solution; (ii) at least one buffer; (iii) an enzyme (e.g., phenylalanine ammonia lyase); or (iv) a combination of at least two of (i) to (iii). It is not necessary or useful to remove the phenylalanine ammonia lyase from the sample solution prior to mixing with polymersomes.

Incubation time of the polymersomes in the sample may vary depending on the nature of the samples. For biological samples, the incubation time is optimally limited to avoid protein degradation. As shown herein, reliable spectroscopic property (i.e. fluorescence intensity and/or absorbance) readings may be made in biological samples after incubation times as short as 2 minutes and up to 15 minutes (see FIG. 2). For non-biological samples, i.e. simple buffers, incubation may be increased while avoiding ammonia evaporation.

As used herein, the terms "body fluid" refer to any fluid from a vertebrate. In a specific embodiment, it refers to a fluid from a mammal. Without being so limited, it includes blood (as is if a NIR dye is used in a fluorescence or absorbance method of the present invention, or after erythrocytes have been removed e.g., by a filter), blood fraction (e.g., serum, plasma), saliva, urine, sweat, semen, peritoneal fluid, fluid from ascites, and cerebrospinal fluid. Certain body fluids may contain ammonia levels or specific amino acid levels that can provide information on the subject (e.g., in terms of the presence or an indication of the presence of a disease or condition in the subject, the effectiveness or non-effectiveness of a treatment or a preventive measure, or the development of side effects resulting from the administration of a medicament). In examples below, certain body fluids have been diluted by a factor selected to fall into the measurement range of the commercial ammonia assay kit used for comparison.

Hence, in specific embodiments where the assayed sample is a body fluid sample, the quantification method may be used for the diagnosis of certain diseases or conditions (e.g., ammonia-associated disease or disorder, or a disease characterized by an increased level of a specific amino acid (e.g., phenylketonuria)). In a more specific embodiment, where the disease or condition is hyperammonemia, it may be used to diagnose/detect/monitor this condition in certain hyperammonemia-inducing treatments (e.g., valproic acid therapy). In other embodiments, it may be used to monitor the efficiency of an anti-hyperammonemia treatment (e.g., hemodialysis) or an anti-phenylketonuria treatment (e.g., a dietary regimen low in phenylalanine).

As used herein an "ammonia-associated disease or disorder" includes hyperammonemia (e.g., induced by impaired liver function or induced by valproic acid therapy), hepatic encephalopathy, liver cirrhosis, acute liver failure, acute-on-chronic liver failure, portosystemic bypass, portosystemic shunting, drug-induced hyperammonemia, inborn deficiency in hepatic ammonia metabolism (primary hyperammonemia), inborn deficiency affecting hepatic ammonia metabolism (secondary hyperammonemia), chronic kidney disease, and ammonia-associated reduced fertility. Blood and its fractions (serum, plasma) can be used as body fluid samples for most ammonia-associated disease or disorders. Saliva can be used as body fluid sample for chronic kidney disease and semen can be used as body fluid sample for ammonia-associated reduced fertility.

Certain diseases are characterized by an increased level of amino acids in the subject's body fluid(s). For example, subjects having phenylketonuria have an increased level of phenylalanine in blood. Phenylketonuria is an inborn error of metabolism which results in low levels of the enzyme phenylalanine hydroxylase (PAH) leading to a decreased metabolism of the amino acid phenylalanine and thereby, an increased blood level of phenylalanine (van Spronsen et al. Lancet Diabetes Endocrinol. 2017; 5:743-756). Such aberrant level of amino acid can indirectly be quantified by first incubating the sample with an ammonia-producing enzyme (e.g., phenylalanine ammonia-lyase for phenylalanine), and then using the ammonia quantification method of the present invention to indirectly determine the amino acid level. Phenylalanine ammonia lyase (EC 4.3.1.24) is an enzyme that catalyzes a reaction converting L-phenylalanine to ammonia and trans-cinnamic acid.

As used herein the terms "subject" refer to a subject who may have levels of ammonia or amino acids in their body fluid sample that would advantageously be quantified by the method of the present invention. It refers to a vertebrate, in a specific embodiment to a mammal and in a more specific embodiment to a human. The polymersomes or compositions of the present invention may also be used in preclinical researches or in veterinary applications and be used in pets or other animals (e.g., pets such as cats, dogs, horses, etc.; and cattle, fishes, swine, poultry, etc.).

In specific embodiments, the subject has an ammonia-associated disease or disorder or phenylketonuria. In another embodiment, the subject undergoes an anti-hyperammonemia treatment (e.g., hemodialysis, liposome-supported peritoneal dialysis) or an anti-phenylketonuria treatment (e.g., a dietary regimen low in phenylalanine).

In another specific embodiment, the subject is suspected of having, or is a likely candidate for having an ammonia-associated disease or disorder or phenylketonuria. Without being so limited, such subjects include for example patients suffering from urea-cycle disorders, hepatic encephalopathy, phenylalanine hydroxylase or tetrahydrobiopterin deficiency, and patients under treatment with hyperammonemia-inducing drugs (e.g., L-asparaginase, valproic acid).

Therefore, in specific embodiments, the body fluid sample may be from any of such subjects.

Depending on the type of assay performed, the "reference ammonia concentration" can be selected from an established ammonia standard level in the specific body fluid sample, a corresponding ammonia concentration determined in a corresponding sample from the subject at an earlier time (e.g., when the method is used to monitor the effectiveness of an anti-hyperammonemia or anti-phenylketonuria treatment or the impact of a hyperammonemia-inducing treatment); an ammonia concentration determined in the corresponding biological fluid of one or more subject(s) known to not being predisposed to certain diseases or conditions (e.g., ammonia-associated disease or disorder or phenylketonuria) and/or known to not having certain diseases or conditions (e.g., ammonia-associated disease or disorder or phenylketonuria) (e.g., when the method is used to diagnose certain diseases or conditions (e.g., ammonia-associated disease or disorder or phenylketonuria). In another embodiment, the reference ammonia concentration is the average or median value obtained following determination of ammonia concentration in a plurality of samples (e.g., samples obtained from several healthy subjects or samples obtained from several subjects having certain diseases or conditions (e.g., ammonia-associated disease or disorder or phenylketonuria)).

As used herein the terms "hyperammonemia-inducing treatment" refer to treatments that may result in hyperammonemia or for which hyperammonemia is a reported side effect. Without being so limited, it refers to valproic acid therapy and L-asparaginase treatment (Ando et al. Biopsychosoc Med. 2017; 11:19; Strickler et al. Leuk Lymphoma 2017).

As used herein, the term "anti-hyperammonemia treatment" refers to any pharmacological (e.g., sodium phenylbutyrate (Buphenyl®), glycerol phenylbutyrate (Ravicti®), sodium phenylacetate and sodium benzoate (Ucephan®, Ammonul®), carglumic acid (Carbaglu®), administration of non-absorbable disaccharide lactulose, rifaximin (e.g., Xifaxan™), spherical carbon adsorbent (AST-120, Kremezin®), and/or administration of transmembrane pH-gradient polymersomes (see e.g., co-pending PCT application No: PCT/IB2017/054966 filed Aug. 15, 2017), Matoori and Leroux supra)); and/or non-pharmacological (e.g., hemodialysis) therapeutic intervention aimed at reducing ammonia levels in body fluids. It also refers to any preventive measure (e.g., preventive administration of lactulose and/or rifaximin, management of spontaneous bacterial peritonitis or gastrointestinal bleeding in HE patients, Vilstrup et al. supra) aimed at preventing an increase in ammonia levels in body fluids. As used herein, the term "anti-phenylketonuria treatment" refers to any pharmacological (e.g., tetrahydrobiopterin, van Spronsen et al. supra) or non-pharmacological therapeutic intervention (e.g., a dietary regimen low in phenylalanine, van Spronsen et al. supra) aimed at reducing phenylalanine levels in body fluids or to any preventive measure (e.g., a dietary regimen low in phenylalanine, van Spronsen et al. supra) aimed at preventing an increase in phenylalanine levels in body fluids.

In specific embodiments where the assayed sample is a soil or wastewater sample, the quantification method may be used for quantifying (e.g., determining the concentration of) ammonia contamination of these matrices (e.g., in case of wastewater contamination with ammonia-containing fertilizers or industrial waste).

Compositions

The polymersomes may be mixed in the samples to be assayed (e.g., for ammonia concentration) in different forms e.g., could be dispersed in an aqueous medium (e.g., water) (potentially with excipients e.g., preservatives) or in their dried form (e.g., deposited on a strip).

The polymersomes of the present invention may be stored as a liquid (e.g., liquid suspension), or solid form (e.g., powder for reconstitution prior to use or deposited on a diagnostic strip).

The present invention also relates to the use of the polymersomes and/or compositions in the preparation of a diagnostic reagent.

The compositions of the invention can contain one or more excipients including, without limitation, preservatives (e.g., sodium azide, sorbic acid/sorbate salts, benzoic acid/benzoate salts, parabens), antioxidants (e.g., ascorbic acid and its salts, erythorbic acid and its salts), and/or salts. When the polymersomes are in a dried form, they could further be formulated with cryoptotectants and/or lyoprotectants (sugars such as trehalose, saccharose and sucrose; polyalcohols such as poly(vinyl pyrrolidone), poly(vinyl alcohol)), and/or bulk agents (e.g., sugars, cellulose derivatives). The polymersomes could also be incorporated on a strip (e.g., diagnostic strip). The support for such strip can be e.g., a polymeric (paper, membrane, plastic) or an inorganic scaffold.

Kits

Also within the scope of the invention are kits comprising (a) at least one type of polymersomes, compositions and/or strips of the present invention; and (b) (i) a solution for hydrating the polymersome (prior to its use); (ii) a buffer for adjusting the pH (and/or osmolarity) of the outer phase or sample to be assayed (e.g., a sample such as a body fluid sample such as blood or blood fraction (e.g., serum, plasma), saliva, urine; tears, semen); (iii) a diluent for diluting the sample to be assayed (e.g., a soil sample); (iv) a fluorescence standard curve (e.g., fluorescence intensity standard curve and/or fluorescence intensity ratio standard curve) and/or an absorbance standard curve; (v) one or multiple solutions of known ammonia concentration (standard ammonia solutions); or (vi) a combination of at least two of (i) to (v), and, eventually, instructions for their use (e.g., for the quantification of ammonia or for the diagnosis of specific diseases or conditions (e.g., ammonia-associated diseases or conditions such as HE or phenylketonuria). The kit can further contain a least one additional (diagnostic) reagent, and/or one or more additional types of polymersomes of the invention. Kits typically include a label indicating the intended use of the contents of the kit. The term label includes any writing, or recorded material supplied on or with the kit, or which otherwise accompanies the kit. The kit may further comprise one or more container(s), reagent(s), administration device(s).

Quantity

The quantity of polymersomes or compositions thereof of the invention to be used in quantification (e.g., determination of concentration) and diagnosis methods will depend on many factors including the polymersome core pH, the polymersome core pH-sensitive dye concentration, the polymersome core acid concentration, the polymersome core osmolarity, the outer phase ammonia concentration, the outer phase pH, and the outer phase osmolarity. The amount of the polymersomes or compositions thereof of the invention will be an amount that effectively quantifies the ammonia in a sample (e.g., body fluid sample, soil, wastewater or buffer solution). Without being so limited, in a specific embodiment, the molar polymersome concentration in the liquid state is estimated to be in the range of 100 nM to 100 mM. In another specific embodiment, the polymersome concentration expressed by the mass concentration of the polymer is between 0.01 mg/mL to 100 mg/mL.

The present invention encompasses any combination of the herein-described polymersomes, or compositions comprising same, in the herein-described ratios, prepared using the herein-described solvent, pH-sensitive dye, and, eventually, acid or acid solutions using the above-described organic phase and water phase mixing techniques.

The use of the terms "a" and "an" and "the" and similar referents in the context of describing the invention (especially in the context of the following claims) are to be construed to cover both the singular and the plural, unless otherwise indicated herein or clearly contradicted by context.

The terms "comprising", "having", "including", and "containing" are to be construed as open-ended terms (i.e., meaning "including, but not limited to") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. All subsets of values within the ranges are also incorporated into the specification as if they were individually recited herein.

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise claimed.

No language in the specification should be construed as indicating any non-claimed element as essential to the practice of the invention.

Herein, the term "about" has its ordinary meaning. In embodiments, it may mean plus or minus 10% of the numerical value qualified. Herein, the term "approximately" has its ordinary meaning. In embodiments, it may mean plus or minus 10% of the numerical value qualified.

Unless otherwise defined, all technical and scientific terms used herein have the same meaning as commonly understood by one of ordinary skill in the art to which this invention belongs.

The present invention is illustrated in further details by the following non-limiting examples.

Example 1: Effect of L-Lysine on Berthelot Reaction-Based Ammonia Quantification Experimental Set-Up.

0.3 mM ammonia without and with 15 mM L-lysine in phosphate-buffered saline (potassium dihydrogen phosphate 1 mM, sodium hydrogen phosphate 3 mM, sodium chloride 155 mM) at pH 7.4 was incubated for 25 minutes at room temperature with the Berthelot reagents (ready-to-use alkaline hypochlorite solution and phenol nitroprusside solution, both obtained from Sigma-Aldrich Chemie GmbH, Buchs, Switzerland). The absorbance of the solution was measured at 636 nm using a spectrophotometer. The presence of L-lysine leads to an underestimation of the ammonia concentration as determined by the Berthelot reaction. Results are shown in FIG. 1 and expressed as mean and standard deviation (n=3).

Example 2: Fluorescence Intensity Ratio-Based Standard Curve of Pyranine-Containing Transmembrane pH-Gradient Polymersomes at Different Ammonia Concentrations in Phosphate Buffer Polymersome Preparation.

PS-b-PEO polymersomes were produced using an oil-in-water (o/w) emulsion method. More particularly, thirty mg of PS-b-PEO (PS/PEO ratio of approx. 1.4, PS(2770)-b-PEO(2000), Advanced Polymer Materials Inc) were dissolved in 100 μL of an organic solvent (dichloromethane). The polymer organic solvent solution (polymer-containing organic solvent phase, i.e. oil phase) was added dropwise to 1 mL citric acid solution 1 mM at pH 5.5 at an osmolality of 300 mOsmol/kg containing 10 mM pyranine (acidic aqueous phase), under sonication in an ice bath so as to form an emulsion having a 9% (v/v) solvent/aqueous phase ratio. The organic solvent was evaporated using a rotary evaporator for at least 5 minutes at 700 mbar at 40° C. At this stage of the process, there is citric acid and the fluorescent dye inside and outside the polymersomes. To remove the unencapsulated fluorescent dye and to exchange the external buffer phase with phosphate-buffered saline (PBS, potassium dihydrogen phosphate 1 mM, sodium hydrogen phosphate 3 mM, sodium chloride 155 mM) at pH 7.4 at 300 mOsmol/kg, the polymersome dispersion was purified on a cross-linked dextran gel filtration column (exclusion limit 5000 g/mol). The resultant polymersomes encapsulated the citric acid solution of pH 5.5 and the fluorescent dye. The fluorescent dye concentration was quantified using the fluorescence emission intensity at 510 nm excited at 413 nm measured by a fluorescence spectrophotometer.

Ammonia Quantification.

Pyranine-containing polymersomes (normalized to a pyranine concentration of 0.057 mM) were incubated with PBS solutions at pH 7.4 containing different ammonia concentrations (0-2 mM) at room temperature. At different time points (2.5; 5; 10 and 15 minutes), the fluorescence emission intensity at 510 nm excited at 455 nm (pH-dependent excitation wavelength) and the fluorescence emission intensity at 510 nm excited at 413 nm (pH-independent excitation wavelength) were measured using a fluorescence spectrophotometer. The fluorescence intensity ratio was determined by normalizing the former to the latter fluorescence emission intensity.

Figure 2:
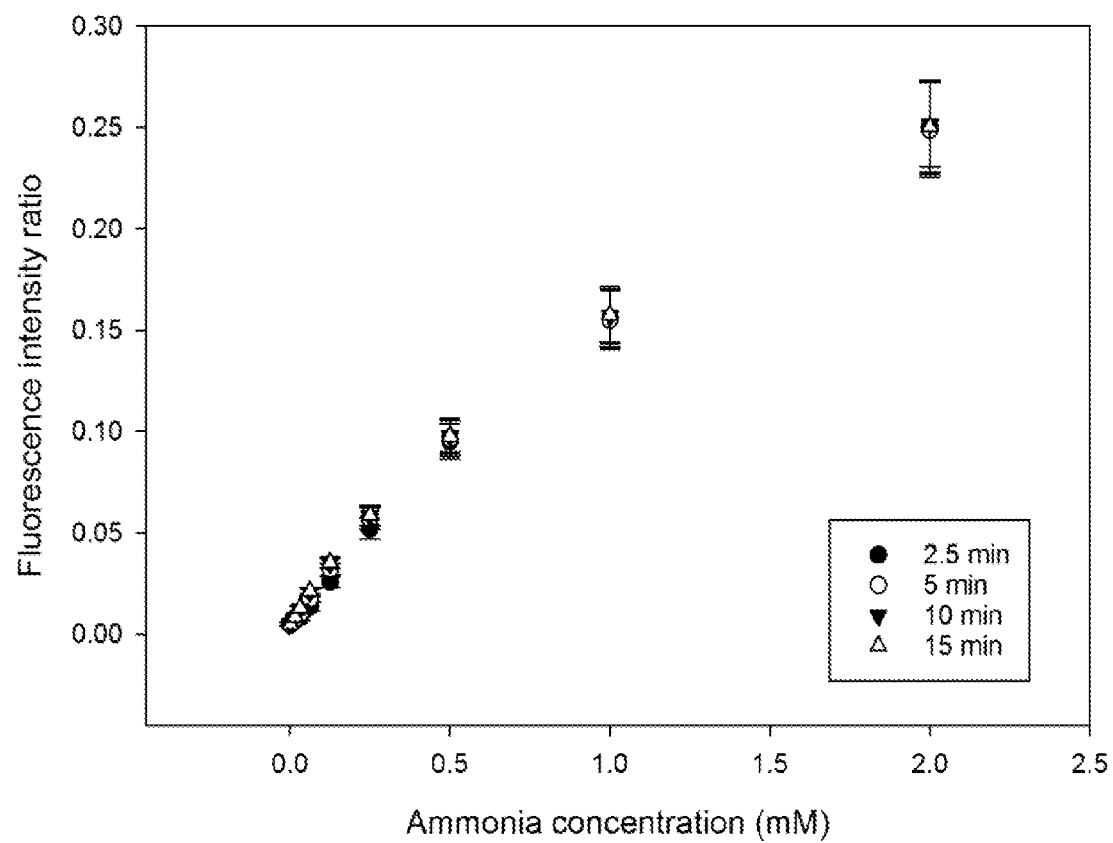
FIG. 2 shows the fluorescence intensity ratio of pyranine-containing PS-b-PEO transmembrane pH-gradient polymersomes at different ammonia concentrations in phosphate buffer. The fluorescence intensity ratio of pyranine-containing PS-b-PEO polymersomes is a function of the ammonia concentration in the medium. Results expressed as mean and standard deviation (n=3).

The fluorescence intensity ratio of pyranine-containing transmembrane pH-gradient PS-b-PEO polymersomes is dependent on the ammonia concentration in the buffer. Results are shown in FIG. 2 and expressed as mean and standard deviation (n=3).

Example 3: Ammonia Quantification by Pyranine-Containing Transmembrane pH-Gradient PS-b-PEO Polymersomes and a Commercial Enzymatic Ammonia Assay in Human Serum Polymersome Preparation.

Fluorescent transmembrane pH-gradient PS-b-PEO polymersomes were produced and purified as described in Example 2 with a modified citric acid concentration of 5 mM and a modified exterior phase in the column-based purification procedure (phosphate buffer 50 mM at pH 7.4 at 300 mOsmol/kg).

Ammonia Quantification.

Pyranine-containing polymersomes (normalized to a pyranine concentration of 0.016 mM) were incubated with commercially available human serum, 0.1 mM ammonia-spiked human serum, and PBS solutions containing different ammonia concentrations (0-0.5 mM) at room temperature. After 10 min, the fluorescence emission intensity at 510 nm excited at 455 nm (pH-dependent excitation wavelength) and the fluorescence emission intensity at 510 nm excited at 413 nm (pH-independent excitation wavelength) were measured using a fluorescence spectrophotometer. The fluorescence intensity ratio was determined by normalizing the former to the latter fluorescence emission intensity. The ammonia concentration of the serum and ammonia-spiked serum were determined by comparison with a linear regression curve (fluorescence intensity ratio standard curve) derived from the fluorescence intensity ratios of the ammonia standards. In addition, the same solutions were analyzed with an enzymatic ammonia kit (Randox Ammonia Assay AM1015, Randox Laboratories Ltd) according to the manufacturer's instructions with the modification of using only 30% of the indicated volumes to enable a measurement in a 96-well plate with a plate reader.

Figure 3:
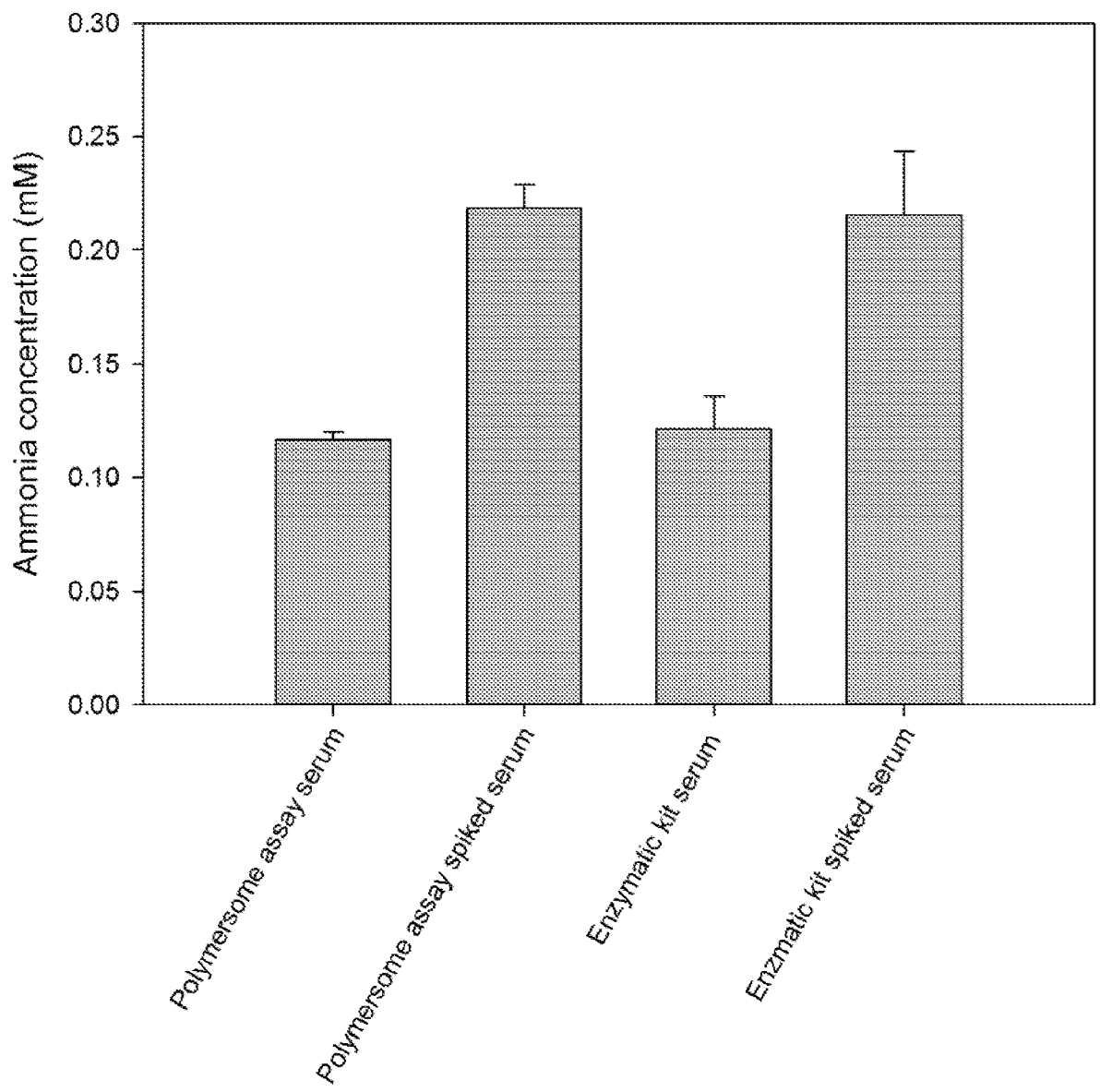
FIG. 3 compares ammonia quantification by fluorescent PS-b-PEO polymersomes and by a commercial enzymatic ammonia assay in human serum. Pyranine-containing transmembrane pH-gradient PS-b-PEO polymersomes were able to quantify ammonia in native and spiked human serum similarly to the enzymatic kit. Results expressed as mean and standard deviation (n=3 for polymersome assay and n=8 for enzymatic kit).

Pyranine-containing transmembrane pH-gradient PS-b-PEO polymersomes were able to quantify ammonia in native and spiked human serum similarly to the enzymatic kit. Results are shown in FIG. 3 and expressed as mean and standard deviation (n=3 for polymersome assay and n=8 for enzymatic kit).

Example 4: Ammonia Quantification by Pyranine-Containing Transmembrane pH-Gradient PS-b-PEO Polymersomes and a Commercial Enzymatic Ammonia Assay in Human Plasma Polymersome Preparation.

Fluorescent transmembrane pH-gradient PS-b-PEO polymersomes were produced and purified as described in Example 3.

Ammonia Quantification.

The ammonia concentration of commercially available human plasma was quantified by pyranine-containing polymersomes and an enzymatic kit as described in Example 3.

Figure 4:
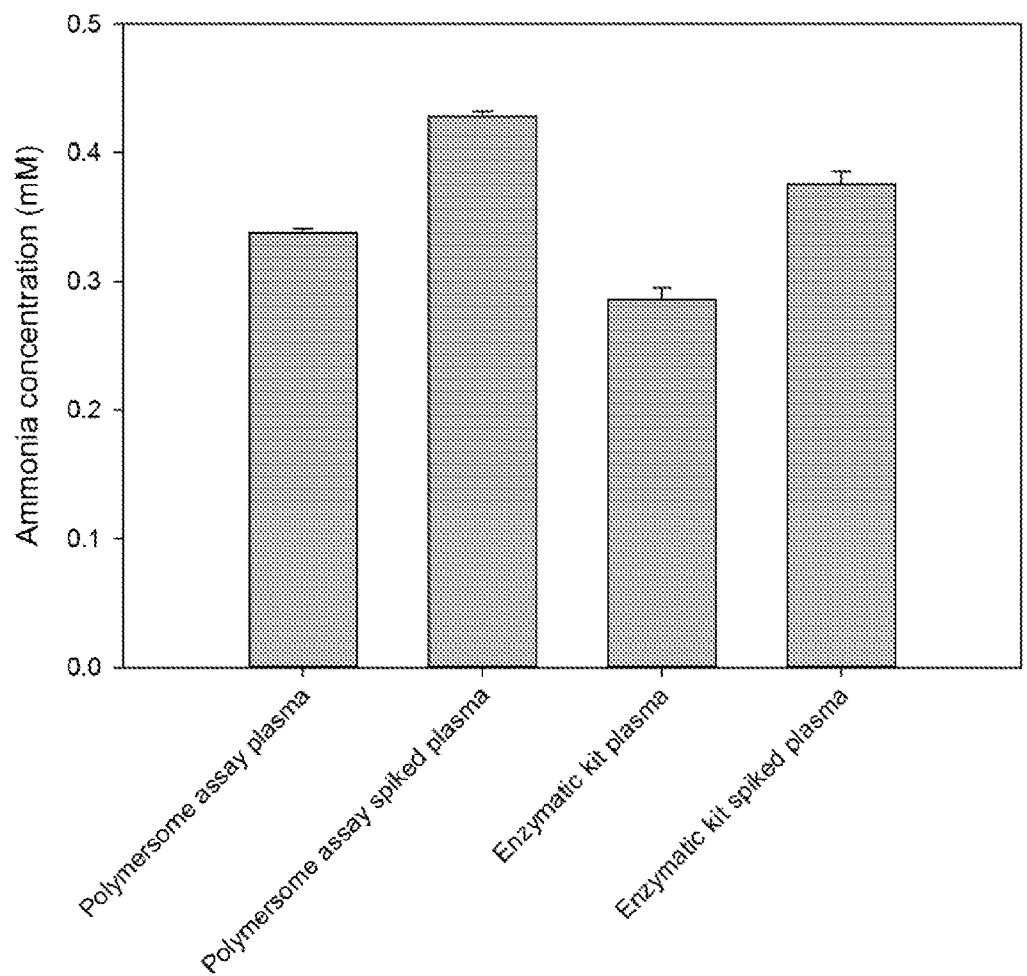
FIG. 4 compares ammonia quantification by fluorescent PS-b-PEO polymersomes and by a commercial enzymatic ammonia assay in human plasma. Pyranine-containing transmembrane pH-gradient PS-b-PEO polymersomes were able to quantify ammonia in native and spiked human plasma similarly to the enzymatic kit. Results expressed as mean and standard deviation (n=3).

Pyranine-containing transmembrane pH-gradient PS-b-PEO polymersomes were able to quantify ammonia in native and spiked human plasma similarly to the enzymatic kit. Results are shown in FIG. 4 and expressed as mean and standard deviation (n=3).

Example 5: Ammonia Quantification by Pyranine-Containing Transmembrane pH-Gradient PS-b-PEO Polymersomes and a Commercial Enzymatic Ammonia Assay in Human Saliva Polymersome Preparation.

Fluorescent transmembrane pH-gradient PS-b-PEO polymersomes were produced and purified as described in Example 3.

Ammonia Quantification.

The ammonia concentration of commercially available human saliva was quantified by pyranine-containing polymersomes and an enzymatic ammonia kit as described in Example 3 with a modified pyranine concentration of 0.017 mM and a modified spiked and non-spiked body fluid preparation (diluting 1:10 (v/v) in PBS and spiking with 0.1 mM ammonia). Finally, the results were multiplied with the dilution factor.

Figure 5:
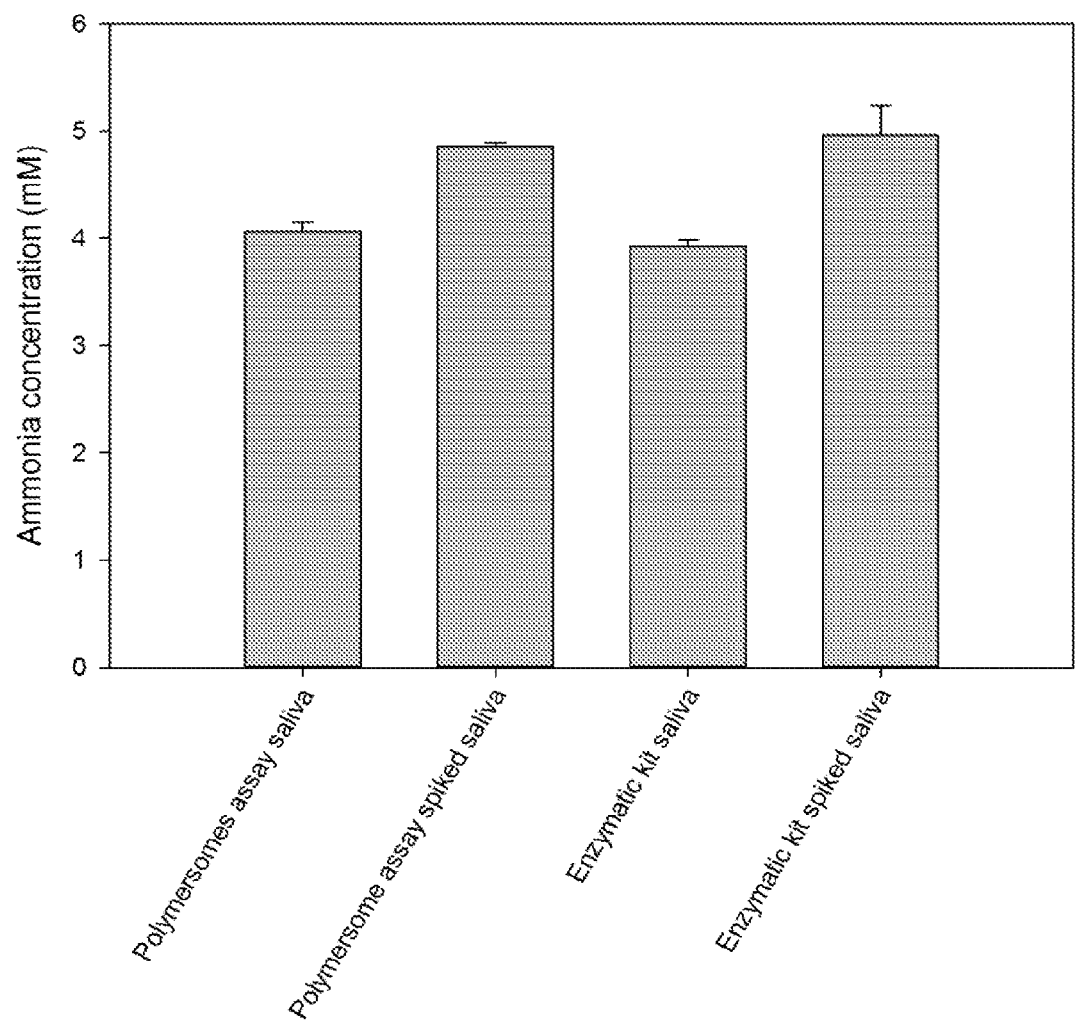
FIG. 5 compares ammonia quantification by fluorescent PS-b-PEO polymersomes and by a commercial enzymatic ammonia assay in human saliva. Pyranine-containing transmembrane pH-gradient PS-b-PEO polymersomes were able to quantify ammonia in native and spiked human saliva similarly to the enzymatic kit. Results expressed as mean and standard deviation (n=3).

Pyranine-containing transmembrane pH-gradient PS-b-PEO polymersomes were able to quantify ammonia in native and spiked human saliva similarly to the enzymatic kit. Results are shown in FIG. 5 and expressed as mean and standard deviation (n=3).

Example 6: Effect of L-Lysine on Pyranine-Containing Transmembrane pH-Gradient PS-b-PEO Polymersome-Based Ammonia Quantification Polymersome Preparation.

Fluorescent transmembrane pH-gradient PS-b-PEO polymersomes were produced and purified as described in Example 2.

Ammonia Quantification.

Pyranine-containing polymersomes (normalized to a pyranine concentration of 0.054 mM) were incubated with a 0.1 mM ammonia-containing PBS solution at pH 7.4 in the presence of 0, 1, 5, and 15 mM L-lysine and in ammonia standards in PBS (0-0.5 mM) at room temperature. After 10 minutes, the fluorescence emission intensity at 510 nm excited at 455 nm (pH-dependent excitation wavelength) and the fluorescence emission intensity at 510 nm excited at 413 nm (pH-independent excitation wavelength) were measured using a fluorescence spectrophotometer. The fluorescence intensity ratio was determined by normalizing the former to the latter fluorescence emission intensity. The ammonia concentration of the L-lysine-free and L-Lysine-spiked ammonia solutions were determined by comparison with a linear regression curve (fluorescence intensity ratio standard curve) derived from the fluorescence intensity ratios of the ammonia standards.

Figure 6:
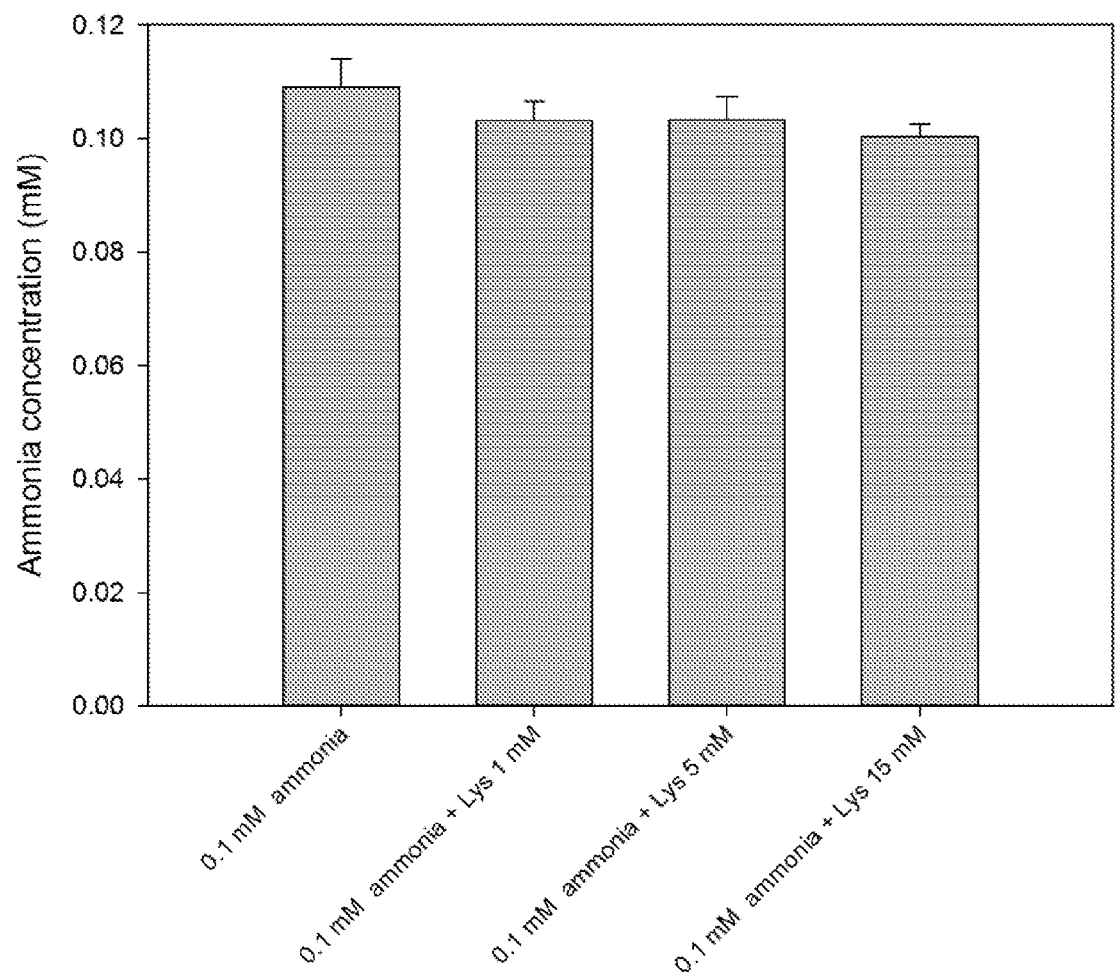
FIG. 6 shows the effect of L-lysine on PS-b-PEO polymersome-based ammonia quantification. The presence of up to 15 mM L-lysine (i.e., 100 times the normal plasma concentration) does not influence the measured ammonia concentration. Results expressed as mean and standard deviation (n=3).

The presence of up to 15 mM L-lysine (i.e., 100 times the normal plasma concentration, Aldred et al. J Autism Dev Disord. 2003; 33:93-97) does not influence the ammonia concentration measured by the fluorescent transmembrane pH-gradient PS-b-PEO polymersomes. Results are shown in FIG. 6 and expressed as mean and standard deviation (n=3).

Example 7: Ammonia Quantification by Pyranine-Containing Transmembrane pH-Gradient PS-b-PEO Polymersomes and a Commercial Enzymatic Ammonia Assay in Human Urine Polymersome Preparation.

Fluorescent transmembrane pH-gradient PS-b-PEO polymersomes were produced and purified as described in Example 3.

Ammonia Quantification.

The ammonia concentration of commercially available human urine was quantified by pyranine-containing polymersomes and an enzymatic ammonia kit as described in Example 5 with a modified spiked and non-spiked body fluid preparation (diluting 1:100 (v/v) in PBS and spiking with 0.1 mM ammonia). Finally, the results were multiplied with the dilution factor.

Figure 7:
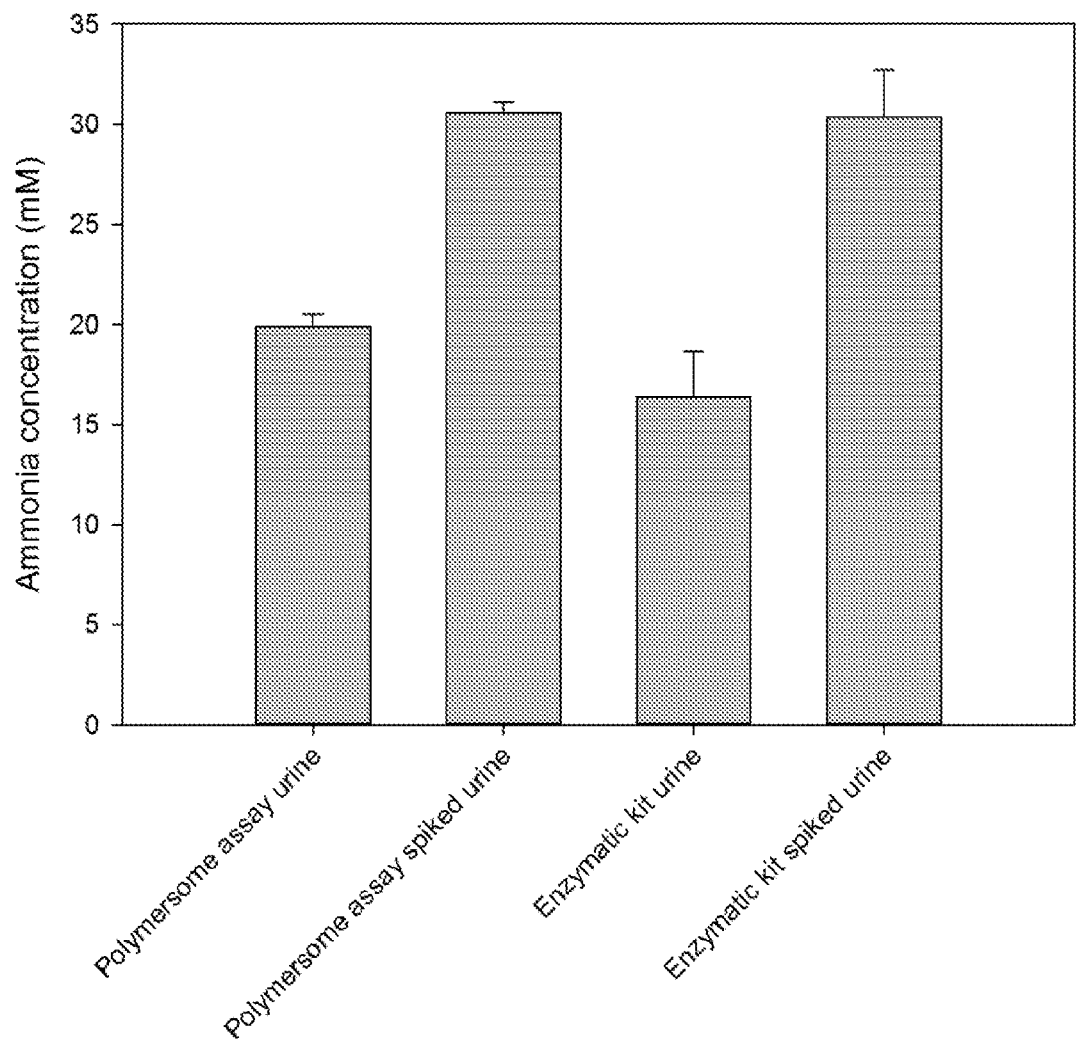
FIG. 7 compares ammonia quantification by fluorescent PS-b-PEO polymersomes and by a commercial enzymatic ammonia assay in human urine. Pyranine-containing transmembrane pH-gradient PS-b-PEO polymersomes were able to quantify ammonia in native and spiked human urine similarly to the enzymatic kit. Results expressed as mean and standard deviation (n=3).

Pyranine-containing transmembrane pH-gradient PS-b-PEO polymersomes were able to quantify ammonia in native and spiked human urine similarly to the enzymatic kit. Results are shown in FIG. 7 and expressed as mean and standard deviation (n=3).

Example 8: Ammonia Quantification by Pyranine-Containing Transmembrane pH-Gradient PS-b-PEO Polymersomes and a Commercial Enzymatic Ammonia Assay in Human Sweat Polymersome Preparation.

Fluorescent transmembrane pH-gradient PS-b-PEO polymersomes were produced and purified as described in Example 3.

Ammonia Quantification.

The ammonia concentration of commercially available human sweat was quantified by pyranine-containing polymersomes and an enzymatic ammonia kit as described in Example 3 with a modified spiked and non-spiked body fluid preparation (diluting 1:10 (v/v) in PBS and spiking with 0.1 mM ammonia). Finally, the results were multiplied with the dilution factor.

Figure 8:
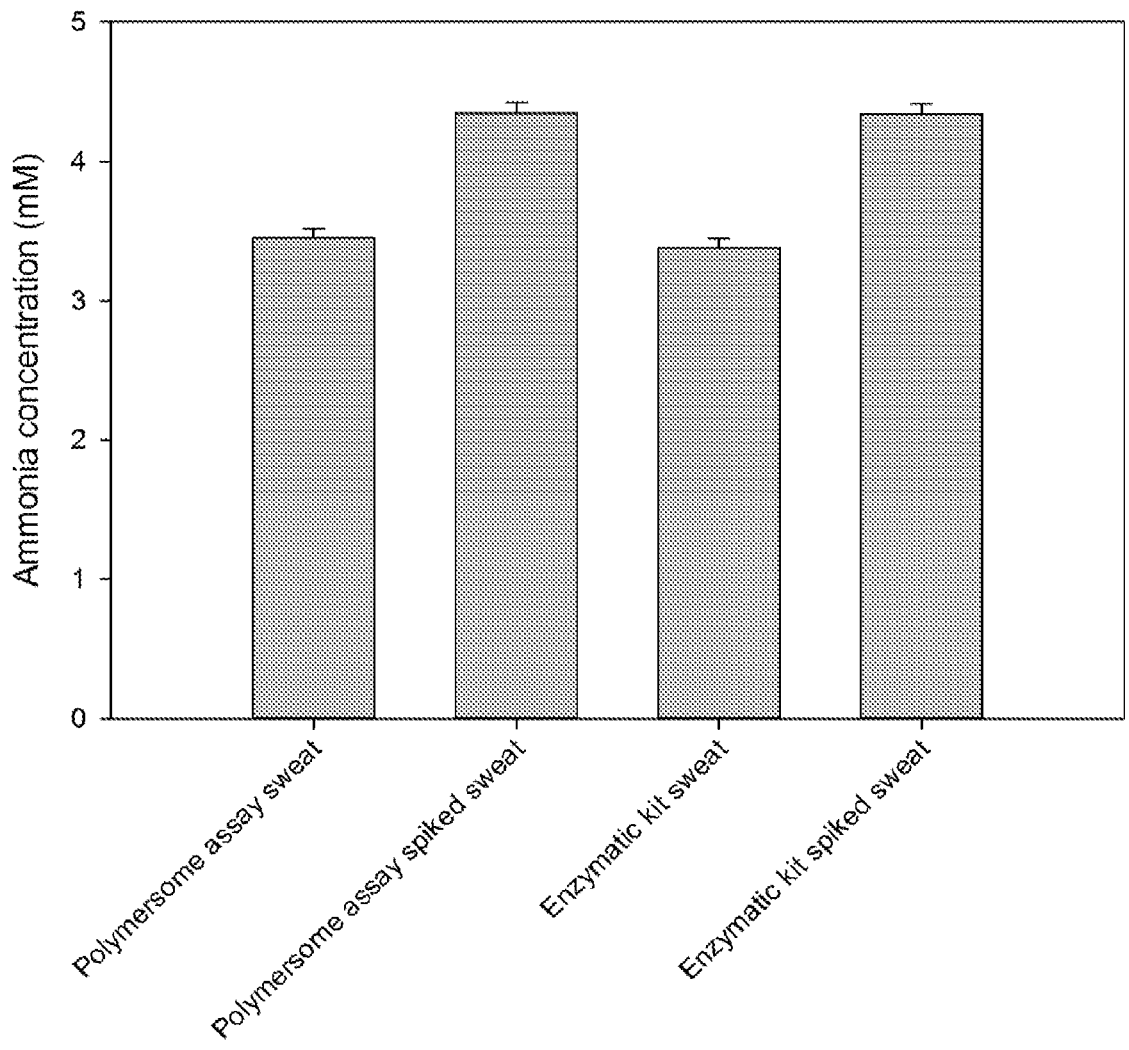
FIG. 8 compares the ammonia quantification by fluorescent PS-b-PEO polymersomes and by a commercial enzymatic ammonia assay in human sweat. Pyranine-containing transmembrane pH-gradient PS-b-PEO polymersomes were able to quantify ammonia in native and spiked human sweat similarly to the enzymatic kit. Results expressed as mean and standard deviation (n=3).

Pyranine-containing transmembrane pH-gradient PS-b-PEO polymersomes were able to quantify ammonia in native and spiked human sweat similarly to the enzymatic kit. Results are shown in FIG. 8 and expressed as mean and standard deviation (n=3).

Example 9: Ammonia Quantification by Pyranine-Containing Transmembrane pH-Gradient PS-b-PEO Polymersomes and a Commercial Enzymatic Ammonia Assay in Human Semen Polymersome Preparation.

Fluorescent transmembrane pH-gradient PS-b-PEO polymersomes were produced and purified as described in Example 3.

Ammonia Quantification.

The ammonia concentration of commercially available human semen was quantified by pyranine-containing polymersomes and an enzymatic ammonia kit as described in Example 3 with a modified spiked and non-spiked body fluid preparation (diluting 1:100 (v/v) in PBS and spiking with 0.1 mM ammonia). Finally, the results were multiplied with the dilution factor.

Figure 9:
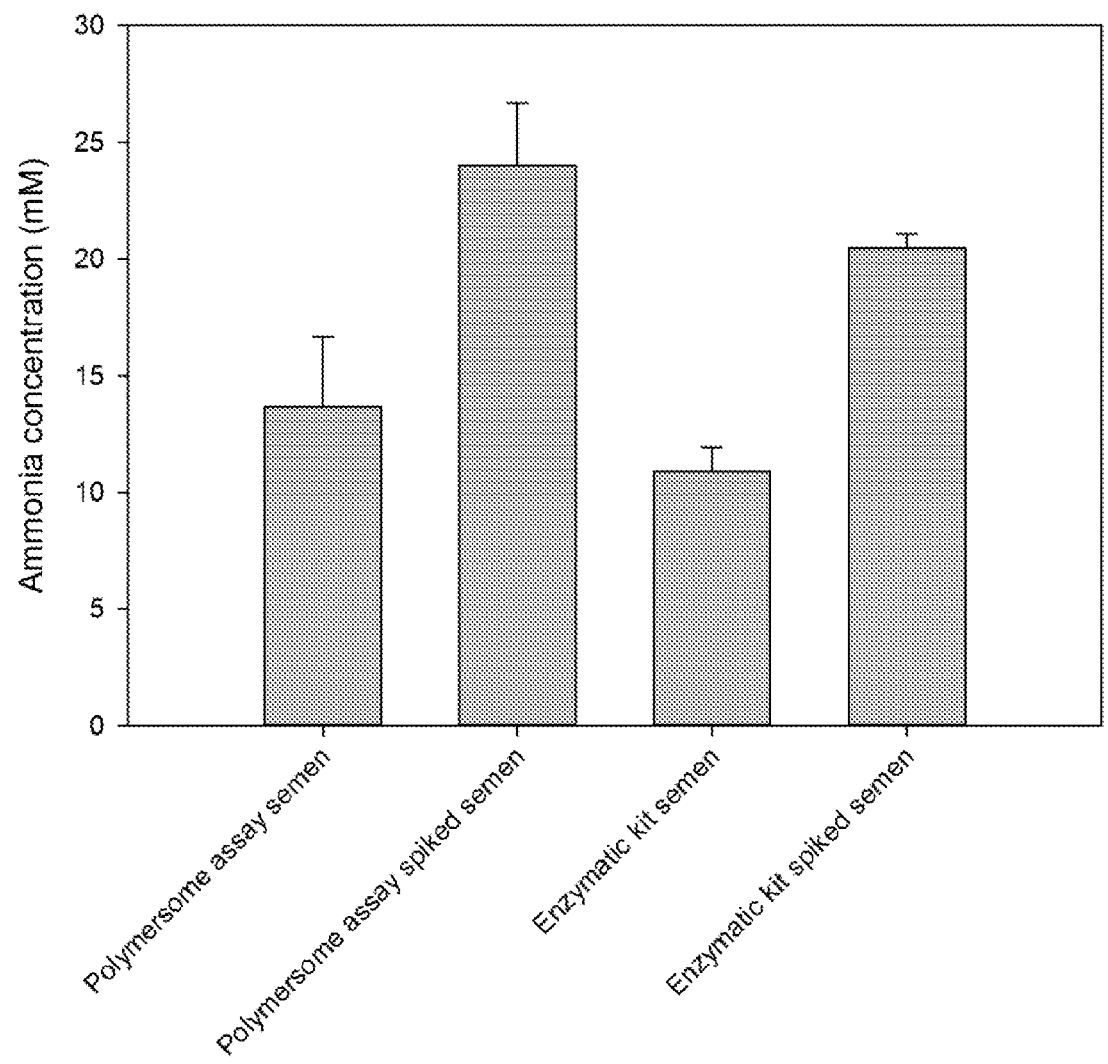
FIG. 9 compares ammonia quantification by fluorescent PS-b-PEO polymersomes and by a commercial enzymatic ammonia assay in human semen. Pyranine-containing transmembrane pH-gradient PS-b-PEO polymersomes were able to quantify ammonia in native and spiked human semen similarly to the enzymatic kit. Results expressed as mean and standard deviation (n=3).

Pyranine-containing transmembrane pH-gradient PS-b-PEO polymersomes were able to quantify ammonia in native and spiked human semen similarly to the enzymatic kit. Results are shown in FIG. 9 and expressed as mean and standard deviation (n=3).

Example 10: Fluorescence Intensity Ratio-Based Standard Curve of Dextran-Conjugated Lysosensor™ Yellow/Blue-Containing Transmembrane pH-Gradient Polymersomes at Different Ammonia Concentrations in Phosphate Buffer Polymersome Preparation.

Fluorescent transmembrane pH-gradient PS-b-PEO polymersomes were produced and purified as described in Example 3 with a modified fluorescent dye (dextran-conjugated Lysosensor™ Yellow/Blue, 10,000 g/mol) at a concentration of 0.01 mM and a modified citric acid solution pH of 2.0.

Ammonia Quantification.

Dextran-conjugated Lysosensor™ Yellow/Blue-containing polymersomes (normalized to a dextran-conjugated Lysosensor™ Yellow/Blue concentration of 0.0012 mM) were incubated with PBS solutions at pH 7.4 containing different ammonia concentrations (0-0.25 mM) at room temperature. After 10 minutes, the fluorescence emission intensity at 540 nm excited at 360 nm (pH-dependent emission wavelength) and the fluorescence emission intensity at 485 nm excited at 360 nm (pH-independent emission wavelength) were measured using a fluorescence spectrophotometer. The fluorescence intensity ratio was determined by normalizing the former to the latter fluorescence emission intensity.

Figure 10:
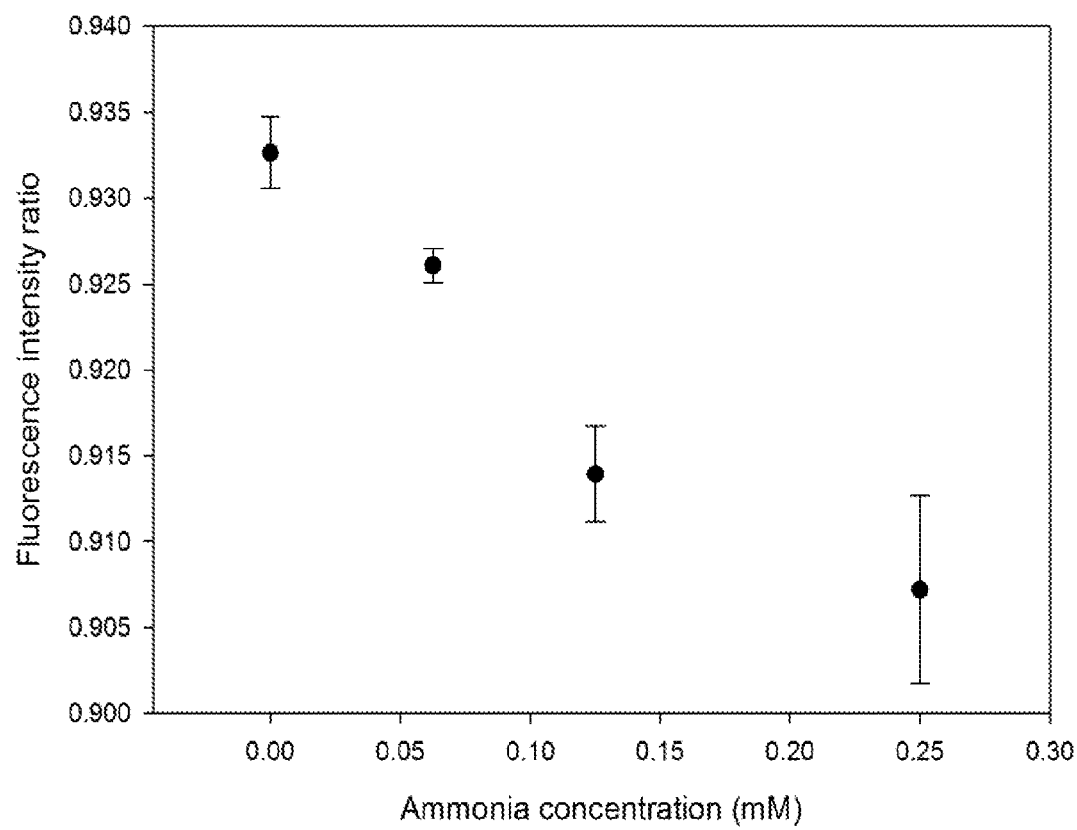
FIG. 10 shows the fluorescence intensity ratio of dextran-conjugated Lysosensor™ Yellow/Blue-containing PS-b-PEO polymersomes at different ammonia concentrations in phosphate buffer. The fluorescence intensity ratio of dextran-conjugated Lysosensor™ Yellow/Blue-containing PS-b-PEO polymersomes is a function of the ammonia concentration in the medium. Results expressed as mean and standard deviation (n=3).

The fluorescence intensity ratio of dextran-conjugated Lysosensor™ Yellow/Blue-containing transmembrane pH-gradient PS-b-PEO polymersomes is dependent on the ammonia concentration in the buffer. Results are shown in FIG. 10 and expressed as mean and standard deviation (n=3).

Example 11: Fluorescence Intensity Ratio-Based Standard Curve of ANTS-Containing Transmembrane pH-Gradient Polymersomes at Different Ammonia Concentrations in Phosphate Buffer Polymersome Preparation.

Fluorescent transmembrane pH-gradient PS-b-PEO polymersomes were produced and purified as described in Example 3 with a modified PS-b-PEO polymer composition (PS/PEO ratio of approx. 1.8, PS(3570)-b-PEO(2000), Advanced Polymer Materials Inc) and a modified fluorescent dye (8-Aminonaphthalene-1,3,6-Trisulfonic Acid, Disodium Salt, ANTS) at a concentration of 10 mM and a modified citric acid solution pH of 2.0.

Ammonia Quantification.

ANTS-containing polymersomes (normalized to an ANTS concentration of 0.008 mM) were incubated with PBS solutions at pH 7.4 containing different ammonia concentrations (0-0.5 mM) at room temperature. After 10 minutes, the fluorescence emission intensity at 520 nm excited at 368 nm (pH-dependent excitation wavelength) and the fluorescence emission intensity at 520 nm excited at 308 nm (pH-independent excitation wavelength) were measured using a fluorescence spectrophotometer. The fluorescence intensity ratio was determined by normalizing the former to the latter fluorescence emission intensity.

Figure 11:
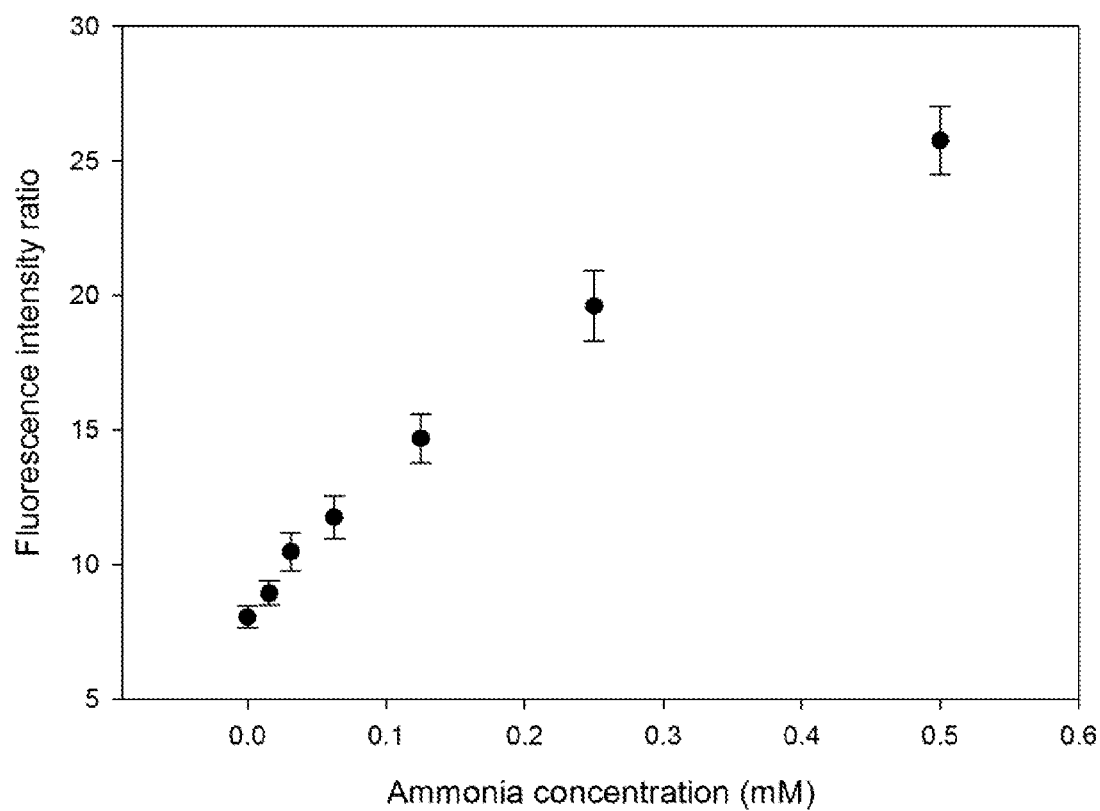
FIG. 11 shows the fluorescence intensity ratio of ANTS-containing PS-b-PEO polymersomes at different ammonia concentrations in phosphate buffer. The fluorescence intensity ratio of ANTS-containing PS-b-PEO polymersomes is a function of the ammonia concentration in the medium. Results expressed as mean and standard deviation (n=3).

The fluorescence intensity ratio of ANTS-containing transmembrane pH-gradient PS-b-PEO polymersomes is dependent on the ammonia concentration in the buffer. Results are shown in FIG. 11 and expressed as mean and standard deviation (n=3).

Example 12: Fluorescence Intensity-Based Standard Curve of IRDye™ 680RD Carboxylate-Containing Transmembrane pH-Gradient Polymersomes at Different Ammonia Concentrations in Phosphate Buffer Polymer synthesis of PS(3700)-b-PEO(2000). PS(3700)-b-PEO(2000) synthesis was carried out by atom transfer radical polymerization (ATRP). Monomethyl PEO(2000) was converted to an ATRP macroinitiator by reaction with 2-bromopropionyl bromide in dry tetrahydrofurane (THF) and further used to polymerize styrene in bulk. Briefly, the ATRP macroinitiator was loaded in a flame dried Schlenk flask, along with copper bromide (CuBr) and 4,4'-dinoyl-2,2'-dipyridyl as the catalyst and ligand, respectively. The Schlenk flask was evacuated and refilled with argon through several cycles to remove oxygen. In a separate flask, styrene was deoxygenated by bubbling argon through it at least for one hour, and then loaded in the Schlenk flask. The mixture was then heated at 115° C. during 16 h and the brown product solution was dissolved in THF, filtered through a basic alumina column and precipitated twice in hexane. The precipitate was filtered and dried under vacuum. The feeding ratio of [monomer]/[initiator] was 50. The PS/PEO composition was determined by nuclear magnetic resonance spectroscopy.

Polymersome Preparation.

Fluorescent transmembrane pH-gradient PS-b-PEO polymersomes were produced and purified as described in Example 3 with a modified PS-b-PEO polymer composition (PS/PEO ratio of approx. 1.9, PS(3700)-b-PEO(2000)), a modified fluorescent dye (IRDye™ 680RD carboxylate) at a concentration of 0.04 mM, a modified citric acid solution concentration of 20 mM and pH of 3.0, and a modified quantification procedure (quantification of the PS-b-PEO polymer concentration by diluting 1:20 (v/v) in dimethylformamide and by determining the absorbance at 271 nm using a UV spectrophotometer and comparing to a PS(3700)-b-PEO(2000) standard curve in dimethylformamide).

Ammonia Quantification.

IRDye™ 680RD carboxylate-containing polymersomes (normalized to a PS-b-PEO concentration of 0.73 mg/mL) were incubated with PBS solutions at pH 7.4 containing different ammonia concentrations (0-0.625 mM) at room temperature. After 10 minutes, the fluorescence emission intensity at 696 nm excited at 666 nm was measured using a fluorescence spectrophotometer.

Figure 12:
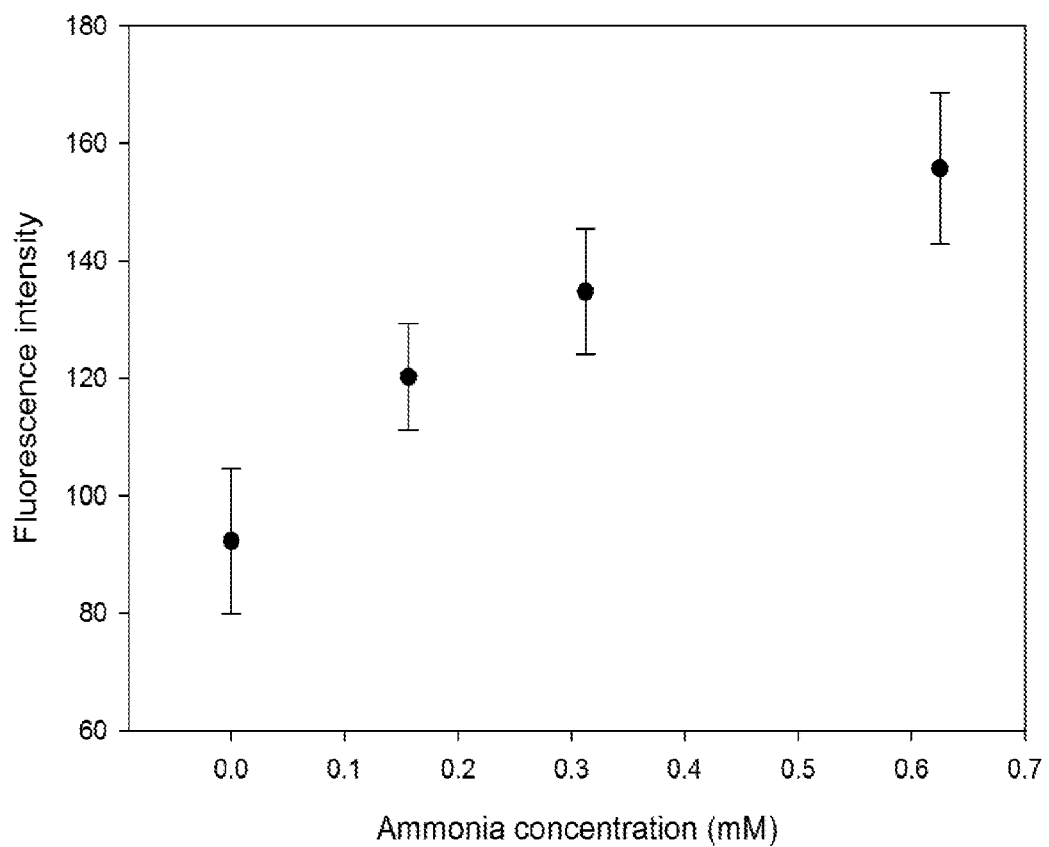
FIG. 12 shows the fluorescence intensity of IRDye™ 680RD-containing PS-b-PEO polymersomes at different ammonia concentrations in phosphate buffer. The fluorescence intensity of IRDye™ 680RD-containing PS-b-PEO polymersomes is a function of the ammonia concentration in the medium. Results expressed as mean and standard deviation (n=3).

The fluorescence intensity of IRDye™ 680RD carboxylate-containing transmembrane pH-gradient PS-b-PEO polymersomes is dependent on the ammonia concentration in the buffer. Results are shown in FIG. 12 and expressed as mean and standard deviation (n=4).

Example 13: Fluorescence Intensity Ratio-Based Standard Curve of Pyranine-Containing Transmembrane pH-Gradient Polymersomes at Different Ammonia Concentrations in Phosphate Buffer in the Absence of an Additional Acid in the Polymersome Core Polymer Synthesis of PS(3700)-b-PEO(2000).

PS(3700)-b-PEO(2000) was synthesized as described in Example 12.

Polymersome Preparation.

Fluorescent transmembrane pH-gradient PS-b-PEO polymersomes were produced and purified as described in Example 3 using a sodium chloride 0.9% (m/V) solution instead of a citric acid solution and with a modified PS-b-PEO polymer composition (PS/PEO ratio approx. 1.9, PS(3700)-b-PEO(2000)). Therefore, the only acid in the core was the fluorescent dye.

Ammonia Quantification.

The ammonia quantification was conducted as described in Example 2 with a modified pyranine concentration (0.017 mM), incubation time (10 min), and ammonia concentration range (0-8 mM).

Figure 13:
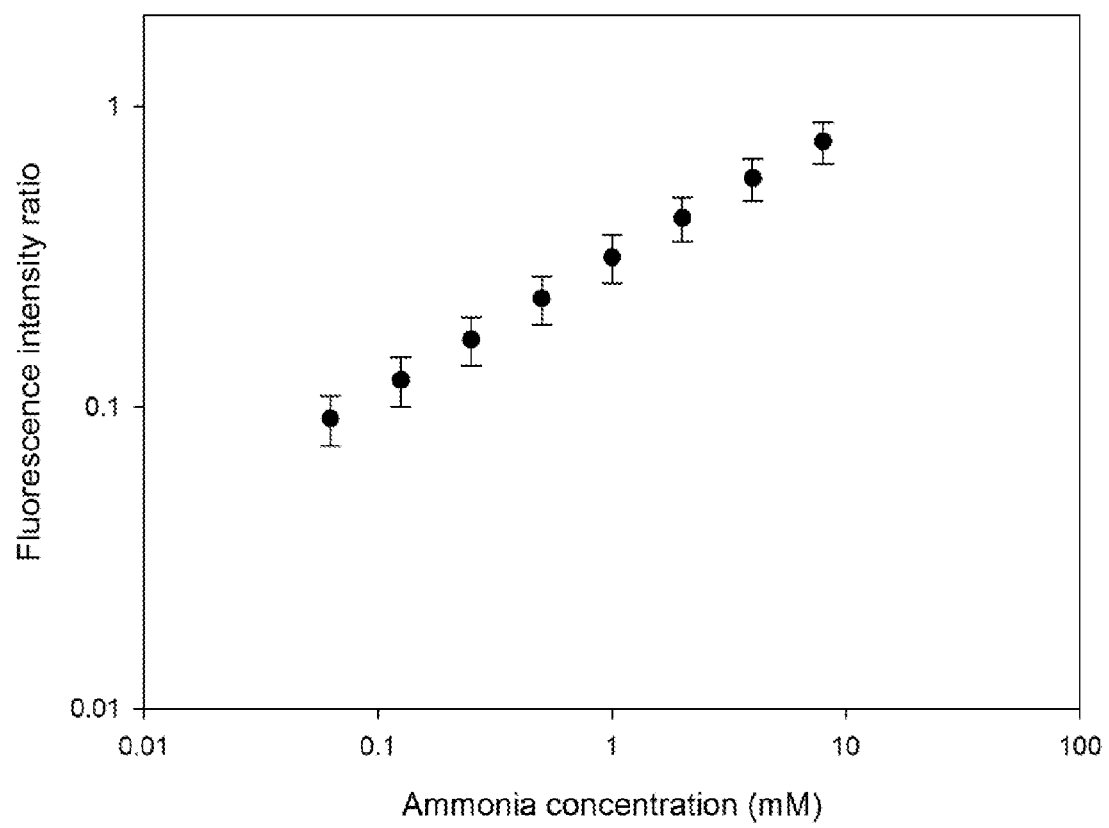
FIG. 13 shows the fluorescence intensity ratio of pyranine-containing PS-b-PEO polymersomes at different ammonia concentrations in phosphate buffer, in the absence of an additional acid in the polymersome core. The fluorescence intensity ratio of pyranine-containing PS-b-PEO polymersomes in the absence of an additional acid in the polymersome core is a function of the ammonia concentration in the medium. Results expressed as mean and standard deviation (n=3).

The fluorescence intensity ratio of pyranine-containing transmembrane pH-gradient PS-b-PEO polymersomes in the absence of another acid in the core is dependent on the ammonia concentration in the buffer. Results are shown in FIG. 13 as a log-log plot and expressed as mean and standard deviation (n=3).

Example 14: Fluorescence Intensity Ratio of Pyranine-Containing Transmembrane pH-Gradient Polymersomes with Modified PS-b-PEO Polymer Compositions at Different Ammonia Concentrations in Phosphate Buffer Polymer Synthesis of PS(2400)-b-PEO(2000).

PS(2400)-b-PEO(2000) synthesis was carried out by ATRP, Monomethyl PEO(2000) was converted to an ATRP macroinitiator by reaction with 2-bromoisobutyryl bromide in dry THF and further used to polymerize styrene in bulk. Briefly, the ATRP macroinitiator was loaded in a flame dried Schlenk flask, along with CuBr and 4,4'-dinoyl-2,2'-dipyridyl as the catalyst and ligand, respectively. The Schlenk flask was evacuated and refilled with argon through several cycles to remove oxygen. In a separate flask, styrene was deoxygenated by bubbling argon through it at least for one hour, and then loaded in the Schlenk flask. The mixture was then heated at 115° C. during three hours and the brown product solution was dissolved in THF, filtrated through basic alumina column and precipitated twice in hexane. The precipitate was filtered and dried under vacuum. The feeding ratio of [monomer]/[initiator] was 28. The PS/PEO composition was determined by nuclear magnetic resonance spectroscopy.

Polymersome Preparation.

Fluorescent transmembrane pH-gradient PS-b-PEO polymersomes were produced and purified as described in Example 3 with modified PS-b-PEO polymer compositions (PS/PEO ratio of approx. 1.2, PS(2400)-b-PEO(2000), and PS/PEO ratio of about 3.0, PS(6000)-b-PEO(2000), Advanced Polymer Materials Inc) and a modified polymer amount for PS(6000)-b-PEO(2000) (10 mg).

Ammonia Quantification.

Pyranine-containing polymersomes (normalized to a pyranine concentration of 0.007 mM for PS(2400)-b-PEO(2000) and 0.002 mM for PS(6000)-b-PEO(2000)) were incubated with PBS solutions containing different ammonia concentrations (0-0.5 mM) and PBS solutions containing 0.2 mM ammonia all at pH 7.4 at room temperature. After 10 min, the fluorescence emission intensity at 510 nm excited at 455 nm (pH-dependent excitation wavelength) and the fluorescence emission intensity at 510 nm excited at 413 nm (pH-independent excitation wavelength) were measured using a fluorescence spectrophotometer. The fluorescence intensity ratio was determined by normalizing the former to the latter fluorescence emission intensity. The ammonia concentration of the 0.2 mM ammonia-containing solution in PBS was determined by comparison with a linear regression curve (fluorescence intensity ratio standard curve) derived from the fluorescence intensity ratios of the ammonia standards.

Figure 14:
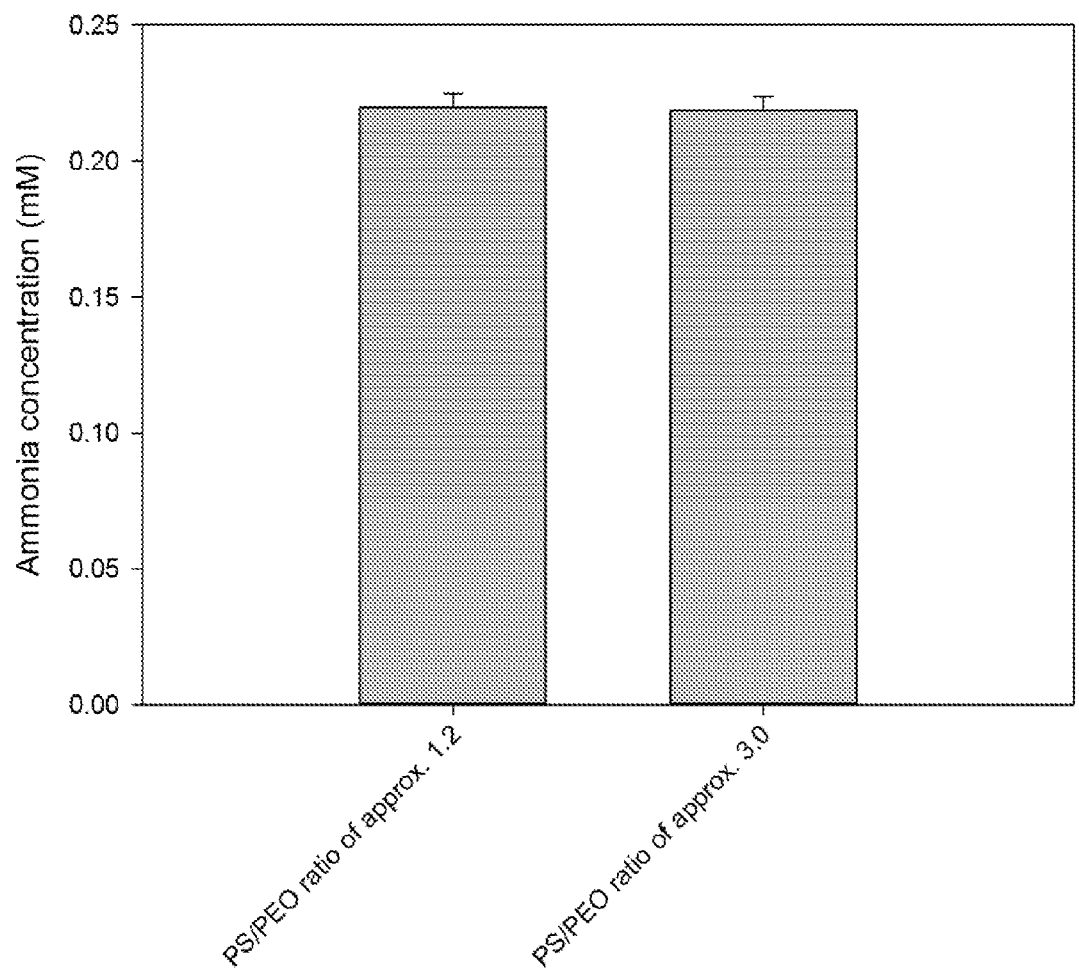
FIG. 14 shows ammonia quantification by pyranine-containing PS-b-PEO polymersomes (PS/PEO ratios of about 1.2 and about 3) in phosphate buffer. Pyranine-containing transmembrane pH-gradient PS-b-PEO polymersomes (PS/PEO ratio of about 1.2 and about 3.0) were able to quantify ammonia in phosphate buffer. Results expressed as mean and standard deviation (n=3).

Pyranine-containing transmembrane pH-gradient PS-b-PEO polymersomes (PS/PEO ratio of about 1.2 and 3.0) were able to quantify ammonia in phosphate buffer. Results are shown in FIG. 14 and expressed as mean and standard deviation (n=3).

Example 15: Phenylalanine Quantification by Pyranine-Containing Transmembrane pH-Gradient PS-b-PEO Polymersomes in Buffer Polymer Synthesis of PS(3700)-b-PEO(2000).

PS(3700)-b-PEO(2000) was synthesized as described in Example 12.

Polymersome Preparation.

Fluorescent transmembrane pH-gradient PS-b-PEO polymersomes were produced and purified as described in Example 3 with a modified PS-b-PEO polymer composition (PS/PEO ratio approx. 1.9, PS(3700)-b-PEO(2000)).

Phenylalanine Quantification.

Commercial phenylalanine ammonia lyase from *Rhodotorula glutinis* (EC number 4.3.1.5, grade I, activity: 0.8-2.0 units/mg protein (1 unit converts 0.001 mmol phenylalanine per min at pH 8.5 at 30° C.), Sigma-Aldrich Chemie GmbH), was purified using centrifugal filtration (cut-off 30 kDa) eight times for 2 min at 15000×g. Phenylalanine ammonia lyase (0.013 mg/mL) was incubated with different phenylalanine solutions (0-1.2 mM, for use as a standard curve) and phenylalanine test solutions (nominal concentration of 0.625 mM) in tris(hydroxymethyl)aminomethane 5 mM at pH 8.5 at 300 mOsmol/kg for 15 min at 30° C. Aliquots of these solutions were subsequently incubated with pyranine-containing polymersomes (standardized to a pyranine concentration of 0.017 mM) in phosphate buffer 50 mM at pH 7.4 (final pH of the dispersion of 7.4) at 300 mOsmol/kg at room temperature. After 10 minutes, the fluorescence emission intensity at 510 nm excited at 455 nm (pH-dependent excitation wavelength) and the fluorescence emission intensity at 510 nm excited at 413 nm (pH-independent excitation wavelength) were measured using a fluorescence spectrophotometer. The fluorescence intensity ratio was determined by normalizing the former to the latter fluorescence emission intensity. Using a phenylalanine fluorescence intensity ratio standard curve, the concentrations of the phenylalanine test solutions were determined to be 0.631±0.022 mM (mean and standard deviation, n=3).

Pyranine-containing transmembrane pH-gradient PS-b-PEO polymersomes can measure the phenylalanine concentration in buffer after incubation with phenylalanine ammonia lyase.

Example 16: Absorbance Ratio-Based Standard Curve of Pyranine-Containing Transmembrane pH-Gradient Polymersomes at Different Ammonia Concentrations in Phosphate Buffer Polymer Synthesis of PS(3700)-b-PEO(2000).

PS(3700)-b-PEO(2000) was synthesized as described in Example 12.

Polymersome preparation. Transmembrane pH-gradient PS-b-PEO polymersomes were produced and purified as described in Example 3 with a modified PS-b-PEO polymer composition (PS/PEO ratio approx. 1.9, PS(3700)-b-PEO (2000)).

Ammonia Quantification.

Pyranine-containing polymersomes (normalized to a pyranine concentration of 0.01 mM) were incubated with PBS solutions at pH 7.4 containing different ammonia concentrations (0-0.5 mM) at room temperature. After 10 minutes, the absorbance was measured at the pH-dependent absorbance wavelengths 450 nm and 405 nm using a spectrophotometer. The absorbance ratio was determined by normalizing the former to the latter absorbance.

Figure 15:
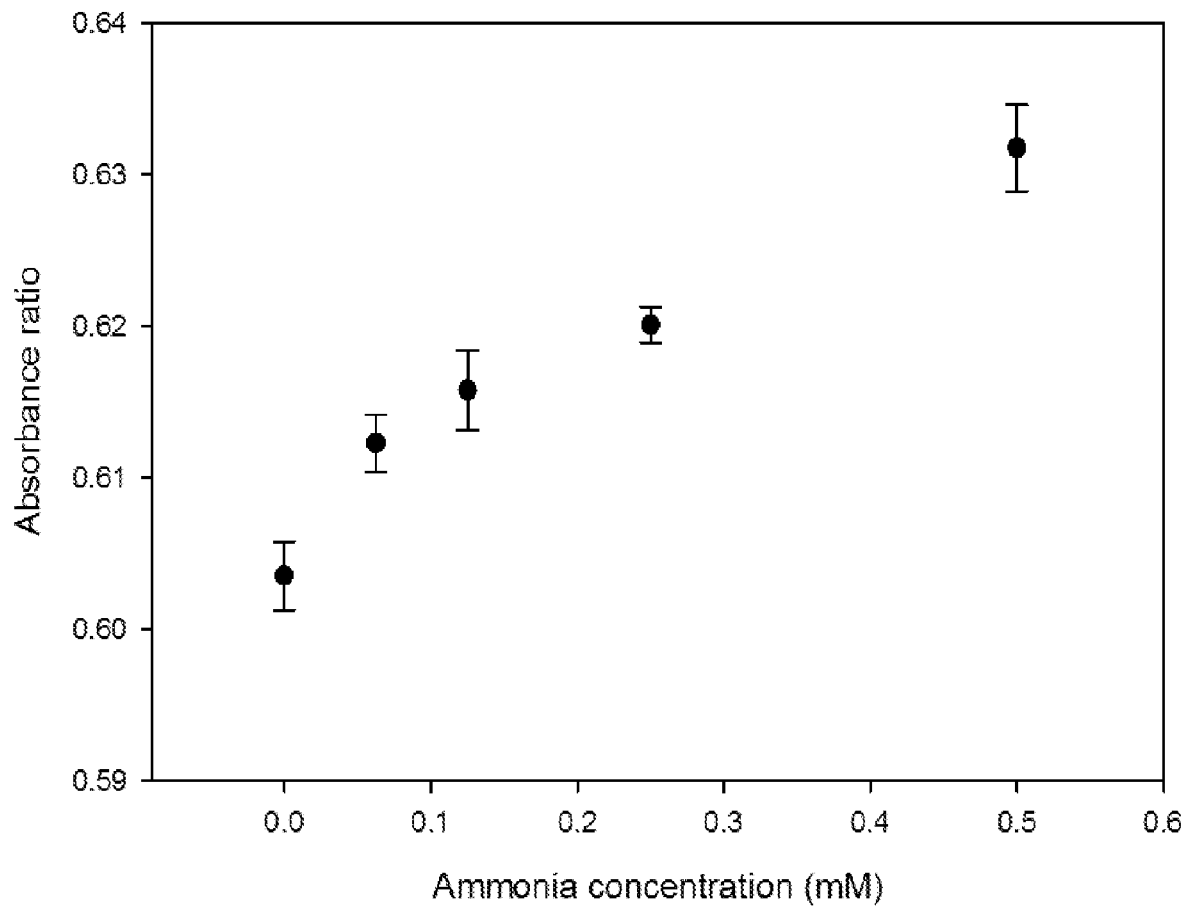
FIG. 15 shows the absorbance ratio of pyranine-containing PS-b-PEO polymersomes at different ammonia concentrations in phosphate buffer. Results expressed as mean and standard deviation (n=3).

The absorbance ratio of pyranine-containing transmembrane pH-gradient PS-b-PEO polymersomes is dependent on the ammonia concentration in the buffer. Results are shown in FIG. 15 and expressed as mean and standard deviation (n=3).

REFERENCES

Agostoni et al. Advanced Functional Materials 2016; 26:8357-8357.
Aldred et al. J Autism Dev Disord. 2003; 33:93-97.
Ando et al. Biopsychosoc Med. 2017; 11:19.
Baliga et al J Indian Soc Periodontol. 2013; 17:461-465.
Barsotti The Journal of Pediatrics 2001; 138:S11-S20.
Blachier et al. Journal of Hepatology 2013; 58:593-608.
Bergmann et al. Pediatrics 2014; 133:e1072-e1076.
Chen et al. J Breath Res. 2014; 8:036003.
Davankov and Tsyurupa Reactive Polymers 1990; 13:27-42.
Goggs et al. Veterinary Clinical Pathology 2008; 37:198-206.
Haugen et al. International Journal of Andrology 1998; 21:105-108.
Hibbard et al. Anal Chem 2013; 85: 12158-12165.
Kano and Fendler BBA Biomembranes 1978; 509:289-299.
Kim et al. International Journal of Andrology 1998; 21: 29-33.
Krack et al. J. Am. Chem. Soc. 2008; 130:7315-7320.
Lukkarinen et al. Metabolism 2003; 52:935-938.
Maalouf et al. Clinical Journal of the American Society of Nephrology 2007; 2:883-888.
Matoori and Leroux ADDR 2015; 90:55-68.
Mook et al. Desalination 2012; 285:1-13.
Mortimer and Mueller, Chemie, $12^{nd}$ edition, Thieme, 2015
Oncescu et al. Lab Chip 2013; 13:3232-3238.
Rose et al. Hepatology 1999; 30:636-640.
Seiden-Long et al. Clinical Biochemistry 2014; 47:1116-1120.
Strickler et al. Leuk Lymphoma 2017; doi: 10.1080110428194.2017.1352090.
van Spronsen et al. Lancet Diabetes Endocrinol. 2017; 5:743-756
Vilstrup et al. Hepatology 2014; 60:715-735.

The invention claimed is:

1. A method of using a polymersome comprising a membrane which comprises a block copolymer of poly(styrene) (PS) and poly(ethylene oxide) (PEO), wherein the PS/PEO molecular weight ratio is higher than 1.0 and lower than 4.0; and (b) a core which encloses an acid and at least one pH-sensitive dye, a composition comprising the polymersome, and at least one excipient, or a strip comprising the composition in solid form, for determining the concentration of ammonia in a sample, comprising:
   (a) contacting the polymersome, composition or strip with the sample;
   (b) determining at least one pH-dependent spectroscopic property in the polymersome- or composition-containing sample or the sample-containing strip; and
   (c) determining the ammonia concentration in the sample using the at least one pH-dependent spectroscopic property by referring to a standard curve.

2. The method of claim 1, wherein the pH-dependent spectroscopic property is (i) a pH-dependent absorbance, the pH-sensitive dye is a pH-dependent absorbance dye and the standard curve is an absorbance standard curve; or (ii) a pH-dependent fluorescence intensity, the pH-sensitive dye is a pH-sensitive fluorescent dye and the standard curve is a fluorescence standard curve.

3. The method of claim 1, wherein (b) further comprises determining at least one pH-independent spectroscopic property or at least one further pH-dependent spectroscopic property in the polymersome- or composition-containing sample or the sample-containing strip to calculate at least one spectroscopic property ratio, and wherein (c) determines the ammonia concentration in the polymersome- or composition-containing sample or the sample-containing strip using the at least one pH-dependent spectroscopic property ratio by referring to a spectroscopic property ratio standard curve.

4. The method of claim 3, wherein the at least one pH-dependent spectroscopic property and the at least one pH-independent spectroscopic property are produced by the same pH-sensitive dye.

5. The method of claim 3, wherein the spectroscopic property is (i) absorbance, and the pH-sensitive dye is a pH-sensitive absorbance dye; or (ii) fluorescence, and the pH-sensitive dye is a pH-sensitive fluorescent dye.

6. The method of claim 1, wherein the pH within the polymersome core is between 2 and 6.5.

7. The method of claim 1, wherein the at least one pH-sensitive dye comprises (i) a hydroxypyrene or one of its pH-sensitive fluorescent derivatives; (ii) a pyridylphenyloxazole or one of its pH-sensitive fluorescent derivatives; (iii) an aminonaphthalene or one of its pH-sensitive fluorescent derivatives; or (iv) cyanine or one of its pH-sensitive fluorescent derivatives.

8. The method of claim 1, wherein the sample comprises a body fluid sample from a subject and/or a buffer.

9. The method of claim 8, wherein the body fluid is a blood or blood fraction sample, a saliva sample, or a semen sample.

10. The method of claim 9, wherein the body fluid has been pretreated with phenylalanine ammonia lyase.

11. The method of claim 9, which is for (i) diagnosing an ammonia-associated disease or disorder or phenylketonuria in the subject, wherein an ammonia concentration in the sample that is higher than a reference ammonia concentration is an indication that the subject has an ammonia-associated disease or disorder or phenylketonuria; or for (ii) monitoring the efficiency of an anti-hyperammonemia or an anti-phenylketonuria treatment, wherein an ammonia concentration in the sample that is lower than a reference ammonia concentration is an indication that the anti-hyperammonemia or anti-phenylketonuria treatment is effective.

12. The method of claim 1, wherein the block copolymer is a diblock copolymer.

13. The method of claim 1, wherein the acid is (i) in a concentration that produces a pH between 1 and 6.5, between 2 and 6.5, between 2 and 6, between 2 and 5.5, or between 3 and 5.5, when the polymersome is hydrated.

14. The method of claim 13, wherein the pH within the aqueous acidic solution is between 1 and 6.5, between 2 and 6.5, between 2 and 5.5, or between 3 and 5.5.

15. The method of claim 1, wherein the at least one pH-sensitive dye comprises 8-hydroxypyrene-1,3,6-trisulfonate (HPTS), dextran-conjugated Lysosensor™ Yellow/Blue, 8-aminonaphthalene-1,3,6-trisulfonate (ANTS), or IRDye™ 680RD carboxylate.

16. The method of claim 1, wherein the acid and the at least one pH-sensitive dye are different molecules.

17. The method of claim 1, wherein the acid is a hydroxy acid.

18. The method of claim 1, wherein the acid is a citric acid.

19. The method of claim 1, wherein the acid and the at least one pH-sensitive dye are the same molecule.

20. The method of claim 1, wherein the polymersome is prepared by a method comprising mixing an organic solvent containing the copolymer with an aqueous phase containing the acid and the at least one pH-sensitive dye.

21. The polymersome of claim 20, wherein the organic solvent is water immiscible or partially water miscible.

22. The method of claim 1, wherein the at least one excipient comprises a preservative, a cryoprotectant, a lyoprotectant, an antioxidant, or a combination of at least two thereof.

23. The method of claim 1, wherein the composition is in a liquid or solid form.

\* \* \* \* \*